US008115167B2

(12) United States Patent
Raznikov et al.

(10) Patent No.: US 8,115,167 B2
(45) Date of Patent: *Feb. 14, 2012

(54) MULTI-BEAM ION MOBILITY TIME-OF-FLIGHT MASS SPECTROMETRY WITH MULTI-CHANNEL DATA RECORDING

(75) Inventors: Valeri V. Raznikov, Moscow (RU); J. Albert Schultz, Houston, TX (US); Thomas F. Egan, Houston, TX (US); Michael V. Ugarov, Houston, TX (US); Agnès Tempez, Houston, TX (US); Gennadiy Savenkov, Moscow (RU); Vladislav Zelenov, Moscow (RU)

(73) Assignee: Ionwerks, Inc., Houston, TX (US)

( * ) Notice: Subject to any disclaimer, the term of this patent is extended or adjusted under 35 U.S.C. 154(b) by 162 days.

This patent is subject to a terminal disclaimer.

(21) Appl. No.: 12/338,529

(22) Filed: Dec. 18, 2008

(65) Prior Publication Data

US 2009/0140140 A1     Jun. 4, 2009

(51) Int. Cl.
*H01J 49/00* (2006.01)
(52) U.S. Cl. .......................................... 250/287; 250/286
(58) Field of Classification Search .................. 250/287, 250/286, 281, 282
See application file for complete search history.

(56) References Cited

U.S. PATENT DOCUMENTS

| | | | |
|---|---|---|---|
| 5,306,910 A | 4/1994 | Jarrell et al. | |
| 5,689,111 A | 11/1997 | Dresch et al. | |
| 5,777,326 A | 7/1998 | Rockwood et al. | |
| 6,278,111 B1 | 8/2001 | Sheehan et al. | |
| 6,630,662 B1 | 10/2003 | Loboda | |
| 7,034,292 B1 | 4/2006 | Whitehouse et al. | |
| 7,196,324 B2 | 3/2007 | Verentchikov | |
| 7,217,919 B2 | 5/2007 | Boyle et al. | |
| 7,429,729 B2 * | 9/2008 | Schultz et al. | 250/287 |
| 2001/0032929 A1 | 10/2001 | Fuhrer et al. | |
| 2002/0100870 A1 | 8/2002 | Whitehouse et al. | |
| 2003/0201389 A1 | 10/2003 | Hartley | |
| 2004/0026613 A1 | 2/2004 | Bateman et al. | |
| 2004/0238755 A1 | 12/2004 | Lee et al. | |
| 2005/0023453 A1 | 2/2005 | Bateman et al. | |
| 2005/0109931 A1 | 5/2005 | Schultz et al. | |
| 2005/0230615 A1 | 10/2005 | Furutani et al. | |
| 2005/0253059 A1 | 11/2005 | Goeringer et al. | |
| 2006/0284080 A1 | 12/2006 | Makarov et al. | |
| 2007/0278397 A1 | 12/2007 | Bateman et al. | |

FOREIGN PATENT DOCUMENTS

| | | |
|---|---|---|
| WO | WO-2004008481 | 1/2004 |
| WO | WO-2005043575 | 5/2005 |

* cited by examiner

*Primary Examiner* — Kiet Nguyen
(74) *Attorney, Agent, or Firm* — Fulbright & Jaworski L.L.P.

(57) ABSTRACT

The content of the invention comprises a concept of multi-beam ion pre-selection from a single sample, coordinated mobility (against the gas flow) separation, cooling ions in supersonic gas flow and mass separation of thus low divergent ions by single or plural compact high-resolution orthogonal time-of-flight mass spectrometers both linear or reflectron type with controlled collision-induced dissociation (CID) and multi-channel data recording for the optimization of sample use in the analysis, and obtaining as much useful information about the sample as possible in a reasonably short time.

22 Claims, 21 Drawing Sheets

MULTI-BEAM ION MOBILITY TIME-OF-FLIGHT MASS SPECTROMETRY WITH MULTI-CHANNEL DATA RECORDING

RELATED APPLICATIONS

This application claims priority to U.S. utility application Ser. No. 11/441,766, filed May 26, 2006 and to U.S. provisional application Ser. No. 60/685,247, filed on May 27, 2005.

TECHNICAL FIELD

The present invention relates generally to instrumentation and methodology for characterization of chemical samples based on ion mobility spectrometry (IMS) and mass spectrometry (MS). Specifically, the invention relates to improved IMS, using the concepts of multi-beam ion pre-selection from a single sample, independent yet coordinated separation of each ion beam by both ion mobility and by single or multiple time-of-flight mass spectrometers (TOFMS) (independently for different beams) each with controllable fragmentation of ion mobility separated ions, and multi-channel data recording in one or a few TOFMS. Specifically, the improvements include simultaneously producing and extracting positive and negative ions from the sample (including the accumulation and post-ionization of neutral species), trapping ions in multiple traps, improved transportation of ions against drift gas flow, a new design of mobility cell/TOFMS interface comprising well collimated supersonic cooled gas flows and an original multi-channel RF-ion guide. Additionally, the technique of multi-beam data recording provides methods for increasing the dynamic range of the measurements and for obtaining additional shape analysis beyond that available from ion mobility alone. These improvements may be used to increase throughput from a sample to downstream instruments and methods. The resulting instruments and methods are useful for qualitative and/or quantitative chemical and biological analysis.

BACKGROUND OF THE INVENTION

An ion mobility spectrometer typically comprises an ionization source, a drift cell, and an ion detector. Examples of an ion detector include a sampling plate, an electron multiplier, or a mass spectrometer. Ion mobility spectrometry separates ions in terms of their mobility in a drift/buffer gas by measuring the ion equilibrium drift velocity. When gaseous ions in the presence of the drift gas experience a constant electric field, they accelerate until the occurrence of a collision with a neutral atom or molecule within the drift gas. This acceleration and collision sequence is repeated continuously. Over time, this microscopic scenario averages the instantaneous velocities over the macroscopic dimensions of the drift tube resulting in the measurement of a constant ion velocity based upon ion size, charge and drift gas pressure. The ratio of the ion velocity to the magnitude of the electric field is defined as ion mobility. In other words, the ion drift velocity ($v_d$) is proportional to the electric field strength (E), where the ion mobility $K=v_d/E$ is a function of ion volume/charge ratio. Thus IMS is a separation technique similar to mass spectrometry. IMS is generally known to have high sensitivity with moderate resolving power. Separation efficiency is compromised when "bands" of ions spread apart as opposed to arriving together at the end of the IM drift tube in a tight, well-defined spatial region.

The resolving power for a uniform or quasi-uniform ion mobility electric field increases as a square root of voltage applied along mobility cell. It would seem that there is not much freedom to increase the resolution. However, the situation may be improved if the ion drift in a gas flow is considered. Ions move against the gas flow only if the field is stronger than a certain value specific for the mobility of the ions. Ions with lower mobility may be stationary or even move in the negative direction (with the gas flow). Therefore, better ion separation can be expected where the time of this separation can be chosen suitable for specific applications and compatible with the time diagram of the ion detector operation. The problem is how to efficiently organize ion mobility separation using gas counter-flow. Most often an ion mobility separation is used with ion sources working under elevated pressure and the source pressure is often used when these ions are introduced into a mobility cell. There may be no gas counter-flow in such an application. On the other hand, drift gas counter-flow is inevitable when IMS is used for analysis of ions created in high vacuum ion sources such as a secondary ion source where secondary ions are created from a surface maintained in high vacuum and must then be moved against a counter-flow of gas into the ion mobility spectrometer. The main problem then is how to overcome the strong counter-flow and preserve ion throughput. It is quite natural to use a time varying electric field to gradually move ions from a pulsed ion formation region against the gas flow and into the IMS. Small ions need a relatively small field to overcome the gas flow without decomposing whereas larger ions can come to the entrance orifice later under the action of a stronger field. At the time of application of the larger field necessary to move the heavier ions, small ions are already inside the mobility cell and are not subjected to the strong field which would otherwise cause their fragmentation. Some separation of ions in addition to the usual mobility separation is achieved in this case, however, it is often rather small, because of the diffusion broadening during the initial ion cloud formation. The gas counter-flow itself is also useful because it prevents neutral species from getting into the mobility cell and degrading its performance by forming non-conductive deposits on the mobility cell electrodes. One of the crucial points for the present invention is the organization of the weaker counter-flow for the low pressure ion sources and purposeful creation of the counter-flow for high pressure ion sources for their interfacing with ion mobility cells.

The combination of an ion mobility spectrometer (IMS) with a mass spectrometer (MS) is well known in the art. In 1961, Barnes et al. were among the first to combine these two separation methods. Such instruments allow for separation and analysis of ions according to both their mobility and mass, which is often referred to as two-dimensional separation or two-dimensional analysis. Young et al. realized that an orthogonal time-of-flight mass spectrometer (oTOFMS) is the most preferred mass spectrometer type to be used in such combination because of its ability to detect simultaneously and very rapidly (e.g. with high scan rate) all masses emerging from the mobility spectrometer. The combination of a mobility spectrometer with an oTOFMS is referred to as an Ion Mobility-oTOFMS. This prior art instrument comprised means for ion generation, a mobility drift cell, an oTOFMS, and a small orifice for ion transmission from the mobility cell to the oTOFMS.

In 2003, Loboda (U.S. Pat. No. 6,630,662) described a method for improving ion mobility separation by balancing ion drift motions provided by the influence of DC electric field and counter-flow of the gas. Using this balance, ions are at first accumulated inside an ion guide, preferably an RF-ion guide, and then, by changing the electric field or gas flow, the ions are gradually eluted from the ion guide to the mass spectrometer. Such type of ion accumulation is restricted to collecting relatively small number of ions due to space-charge effect. It also has some limitation in ion mass-to-charge (m/z) range because RF-focusing for a given RF-voltage has decreasing efficiency for larger mass ions. Increasing RF-voltage in this case is limited due to the possibility of glow discharge at high voltages. For at least these reasons, this method has significant resolving power limitations, particularly for large mass ions. The time of ion accumulation and their storage in RF-ion guide should not be too long, otherwise ions would be partially lost due to diffusion into rods or walls confining the gas flow. The instrumental improvements disclosed below eliminate these drawbacks.

Use of MS as a detector enables separation based on mass-to-charge (m/z) ratio after the separation based on ion mobility. Shoff and Harden pioneered the use of Mobility-MS in a mode similar to tandem mass spectrometry (MS/MS). In this mode, the mobility spectrometer is used to isolate a parent ion and the mass spectrometer is used for the analysis of fragment ions (also called daughter ions), which are produced by fragmentation of parent ions. Below this specific technique of operating a Mobility-MS is referred to as Mobility/MS, or as Mobility-TOF if the mass spectrometer is a TOFMS-type instrument. Other prior art instruments and methods using sequential IMS/MS analysis have been described (see, e.g., McKight, et al. Phys. Rev., 1967, 164, 62; Young, et al., J. Chem. Phys., 1970, 53, 4295; U.S. Pat. Nos. 5,905,258 and 6,323,482 of Clemmer et al.; PCT WO 00/08456 of Guevremont) but none combine the instrumental improvements disclosed here. When coupled with soft ionization techniques and the sensitivity improvements obtained through the use of the drift cell systems disclosed herein, the IMS/MS systems and corresponding analytical methods of the present invention offer significant analytical advantages over the prior art, particularly for the analysis of macromolecular species, such as biomolecules.

One challenge when building a Mobility-MS system is to achieve high ion transmission from the mobility region into the MS region. It is at this interface that earlier uses of linear fields appear incongruous with the goal of maximizing ion throughput across the IMS/MS interface. The mobility section operates at typical pressures between 1 mTorr and 1000 Torr whereas the MS typically operates at pressures below $10^{-4}$ Torr. In order to maintain this difference in pressure it is necessary to restrict the cross-section of the exit orifice of the IM drift cell so that the region between the IM and the MS can be differentially pumped. Typically this orifice cross section is well below 1 $mm^2$. Hence it is desirable to focus the ions into a narrow beam before they reach the interface. Another important property of ion beam coming into MS is the beam divergence, or the kinetic energy of ion motion in the plane orthogonal to the direction of their travel. This is the main factor responsible for the quality of mass spectra obtained in the orthogonal TOFMS. It is a subject of the present invention to achieve good ion beam properties by using a thin dielectric coating of the electrodes followed by controlled charging of this coating. It allows the use of a channel instead of an exit orifice with sharp edges for the IM drift cell and to form low divergent supersonic gas flow where ions could be significantly cooled to have an average energy of their side motion corresponding to a few ° K.

In 1997, Brittain, et al. (U.S. Pat. No. 5,633,497) described the coating of the interior surfaces of an ion trap or ionization chamber with an inert inorganic non-metallic insulator or semiconductor material for the passivation of the surfaces in order to minimize absorption, degradation or decomposition of a sample in contact with the surface U.S. Pat. No. 6,600,155 to Andrien et al., teaches the coating of a surface in time-of-flight pulsing region with a dielectric film (among other types of films) for improving ion beam properties before orthogonal extraction of ions into the drift region of a time-of-flight mass spectrometer Whitehouse (U.S. Pat. No. 6,707,037) proposed the extraction of ions of both signs from a MALDI target directly located inside gas-filled RF-multi-pole ion guide, to concentrate them along the axis of the guide, and send them in opposite directions under the influence of an axial electric field for subsequent mass analysis.

Park (US Patent Application No. 2004/0149902 A1) proposed the use of a multi-pole RF-ion guide to insert ions from a number of ion sources into analytical devices including mass spectrometers and mobility spectrometers. In 2002 Moini and Jiang in U.S. Pat. No. 6,465,776 described the insertion of ions from multiple electrospray capillaries through one quadrupole RF-ion guide where ion beams are mixed into TOFMS. However, multi-channel data recording was not disclosed.

U.S. Pat. No. 5,763,865 to Kaersdorf et al. disclosed a method and apparatus for quantitative non-resonant photo-ionization of neutrals. A time-of-flight mass spectrometer with novel ion mirror for separation of different ion beams is described. Eriksson, in U.S. Pat. No. 6,683,302 described an electrospray ion source wherein heating of droplets emerging from the electrospray capillary under the influence of strong electric field is provided by a microwave field between the spray tip and mass analyzer. U.S. Patent Application No. 20030226750 of Fenn suggests the use of AC voltage to produce charged droplets from the solution emerging from a conducting capillary instead of DC voltage used in conventional electro-spray ion sources. It was disclosed that the flow of the droplets for 60 Hz 5 kV AC voltage is similar to that of a conventional electrospray (ESI) ion source. In 2003 Ranasinghe et al. (US Patent Application No. 2003/0001090) proposed to split the liquid flow from some separation device into two approximately equal streams and direct them into two ion spray sources—the first one producing positive ions and the second one producing negative ions. Two TOFMS systems are used to record positive and negative ions separately.

In 2002, Berggren, et al. (US Patent Application No. 2002/0166961) described a charged droplet source for mass spectrometer with the focusing of droplets and ions using an aerodynamic lens. This lens is a sequence of coaxial apertures where the gas flow comes through orifices with decreasing diameter so that charged particles are focused to some extent.

In 2003 Cornish et al. (U.S. Pat. No. 6,580,070) suggested to combine several relatively simple coaxial TOFMS systems with MALDI or laser ablation ion sources. One array located inside a vacuum chamber provides high throughput analysis of several samples or one large sample in different points. In 2004 Hobbs, et al. (US Patent application No. 20040217279) described multianalyzer mass-spectrometer for the parallel analysis of multiple samples preferably coupled with fluid phase separation techniques All of the above-referenced U.S. patents and published U.S. patent applications are incorporated by reference as though fully described herein.

Although much of the prior art resulted in improvements in ion focusing, separation and in ion throughput from ion source to the mobility cell and to the mass spectrometer in tandem instruments, there is room for additional improvement in all these directions. The inventors describe herein a concept and designs of multi-beam ion mobility and mass separations with multi-channel data recording which result in variety of instrumental embodiments to provide improved ion production from investigated samples, their separation and measurements.

BRIEF SUMMARY OF THE INVENTION

The present invention is directed to a system and method for mass spectrometric analysis of samples. The present invention mainly deals with systems and methods using ion mobility drift cells for transporting ions through a high pressure gas to a TOF MS. The following concepts are described in various embodiments of the present invention: (i) multi-beam ion pre-selection from a single sample, (ii) coordinated mobility and mass separation of ions by single or plural TOFMS (independently for different beams) with controllable, on-demand ion fragmentation, and (iii) multi-channel data recording to increase the efficiency of sample use in the analysis or to obtain as much useful information as possible about the sample in a reasonably short time. Specifically, the improvements lie in (i) extracting or producing both positive and negative ions from the sample (ii) accumulation and post-ionization of neutrals, (iii) trapping of ions in a plurality of traps, (iv) improved ion transportation against the gas flow into mobility cells, and (v) a new design for a mobility cell/TOFMS interface comprising well collimated supersonic cooled gas flows into a unique multi-channel RF-ion guide. In comparison to conventional methods, improvement (v) provides significantly lower divergence of the ion beam entering the TOF MS which in turn improves the mass resolution and mass accuracy of the TOFMS measurement. Because of this new approach, the divergence of the ion beam is low enough to use a simple linear TOFMS instead of more complicated reflectron type TOFMS and still obtain mass resolution in the range of several thousands. It is possible also to decrease further the divergence of the ion beam by using parabolic (or quasi-parabolic) ion mirror made of conductor coated by a variety of non-conducting (or poorly conducting) thin films. Parabolic mirrors include parabolic mirrors, cylindrical parabolic mirrors, and other parabolic variations. It is possible in this case to achieve resolving powers of more than 10000 for small (~20 cm length) linear time-of-flight mass spectrometer. The multi-channel data recording system not only acquires separate data from each ion mobility channel but also provides an increased dynamic range of for ion intensity measurements within the TOFMS. It also allows the determination of additional characteristics of ions such as velocity and divergence, which in conditions close to equilibrium with gas flow, provides a direct estimation of the charge state. These advantages of multi-channel data recording may also be implemented in a simple way in a linear TOFMS. These improvements may be used to increase throughput from an ion source to downstream instruments and they may also provide additional information about the samples beyond merely summing of the data for different ion beams. The resulting instruments and methods are useful for qualitative and/or quantitative chemical and biological analysis.

In the present invention it is taught to accumulate both negative and positive ions from MALDI target or from other sources (secondary ion sources, fast atom bombardment sources, electrospray source, atmospheric pressure ionization sources) in RF multi-pole ion traps, which gives a possibility to collect ions from the target while the previous portion of ions is moving and being recorded. It may give better and more effective conditions for producing and collecting ions and thus higher sensitivity. After ion accumulation the operation of the RF-multi-pole ion traps is altered so that ions of both sign ions can be inserted against the buffer gas flow into the two opposing arrays of multi-channel ion mobility cells. After the insertion of the largest desired ions into the entrance plane of a desired ion mobility channel, the cycle of ion accumulation is repeated once again. The main advantage of such ion insertion against the gas flow compared to prior art is the significant increase of mobility resolution and better control over the time of mobility separation.

In one aspect of the present invention, there is an apparatus for analyzing a flow of gaseous ions or mixture of gaseous ions and gaseous neutral species, the apparatus comprising an ion mobility assembly comprising an ion trapping region comprising a plurality of ion traps to receive the flow of gaseous ions or mixture of gaseous ions and gaseous neutral species; a plurality of parallel mobility tubes, each of the mobility tubes fluidly coupled to the ion trapping region; optionally, a plurality of parallel CID tubes, each of the CID tubes fluidly coupled to at least one of the mobility tubes; optionally, a plurality of parallel exit tubes, each of the exit tubes comprising at least one electrode and being fluidly coupled to at least one of the CID tubes or to at least one of the mobility tubes; and, at least one multi-channel RF ion guide fluidly coupled to at least one of the exit tubes, at least one of the CID tubes, or at least one of the mobility tubes; the ion mobility assembly having a separation axis in a first direction; and, at least one TOFMS fluidly coupled to the ion mobility assembly, the TOFMS comprising a position sensitive detector. In some embodiments, the ion trapping region is operable under a pressure of about 0.1 to about 10 Torr. In some embodiments, the plurality of ion traps comprises are least one RF ion trap. In some embodiments, the plurality of ion traps comprises at least one DC field trap. In some embodiments, the apparatus further comprises voltage grids between the ion traps and the first mobility tubes. In some embodiments, the apparatus further comprises at least one collimating electrode between the ion traps and the first mobility tubes. In some embodiments of the apparatus, the mobility tubes comprise a front element operable at variable voltage biases. In some embodiments, the front element comprises a discrete section of capillaries, a microchannel plate section, or a combination thereof. In some embodiments, the one or more of the mobility tubes and/or CID tubes comprises a surface which is at least partially coated with a thin dielectric film. In some embodiments, the at least one of the multi-channel RF ion guides comprises multiple pairs of rods and confining plates. In some embodiments, the apparatus further comprises at least one ion mirror between the at least one multi-channel RF ion guide and the at least one TOFMS. In some embodiments comprising at least one mirror, the at least one ion mirror comprises a conductor coated by a dielectric film. In some embodiments comprising at least one mirror comprising a conductor coated by a dielectric film, the at least one ion mirror comprises a parabolic mirror, a cylindrical parabolic mirror, or a quasi-parabolic mirror; and, a flat mirror. In some embodiments comprising at least one mirror comprising a conductor coated by a dielectric film, the ion mirror comprises a surface that is charged. In some embodiments comprising at least one mirror comprising a conductor coated by a dielectric film wherein the ion mirrors comprise thin metallic strips, the strips being alternately biased by positive and negative voltages, the voltages being RF voltages or DC voltages. In some embodiments comprising at least one mirror comprising a conductor coated by a dielectric film, the ion mirrors comprise electrode strips on a piezoelectric film surface. In some embodiments of the apparatus, the apparatus further comprises an ion interface assembly located at a high pressure/high vacuum interface between the ion mobility assembly and the at least one TOFMS. In some embodiments wherein the apparatus further comprises an ion interface assembly located at a high pressure/high vacuum interface between the ion mobility assembly and the at least one TOFMS, the ion interface assembly comprises an entry electrode, one or more focusing electrode assemblies, at least one ion mirror with a dielectric coating, a sectioned tube coated with a dielectric film, and a field-free tube coated with a dielectric film and having a larger diameter than the sectioned tube. In some embodiments of the apparatus, the TOFMS comprises a multi-channel detector. In some embodiments, the TOFMS is an oTOFMS. In some embodiments, the TOFMS is a LoTOFMS. In some embodiments, the TOFMS is a gridless LoTOFMS. In some embodiments, the ion mobility assembly comprises more than one ion mobility assembly and wherein one or more pairs of the more than one ion mobility assembly are opposed pairs. In some embodiments, the apparatus further comprises repeller electrodes divided into strips, the repeller electrodes located between the ion traps and the mobility tubes. In some embodiments, the apparatus further comprises an orthogonal collection region. In some embodiments comprising an orthogonal collection region, the orthogonal collection region comprises one or more voltage grids. In some embodiments, the apparatus further comprises a source for the generation of the flow of gaseous ions or mixture of gaseous ions and gaseous neutral species, the source being fluidly coupled to the ion mobility assembly, and the source being configured to generate the flow in a direction that is orthogonal to the first direction. In some embodiments of that apparatus having an orthogonal source and ion mobility assembly, the source further comprises means for post-ionization of gaseous ions or gaseous mixtures of ions. In some embodiments of that apparatus having an orthogonal source and ion mobility assembly, the source is selected from the group consisting of a laser desorption source, a cluster bombardment source, a secondary ion source, an electrospray ionization source, photoionization source, a pneumo-spray source, an atmospheric pressure ionization source, and any combination thereof. In some embodiments wherein the source is a laser desorption source, the laser desorption source is a matrix assisted laser desorption ionization source. In some embodiments of the apparatus wherein a source is present, the source is a secondary ion source. In some embodiments employing a secondary ion source, the apparatus further comprises an electrically conducting input tube having an entrance region and an exit region, the entrance region fluidly coupled to the source and the exit region fluidly coupled to the ion trapping region. In some embodiments employing a secondary ion source and further comprising an electrically conducting input tube having an entrance region and an exit region with the entrance region fluidly coupled to the source and the exit region fluidly coupled to the ion trapping region, the electrically conducting input tube has an internal surface comprising a dielectric film coating. In some embodiments employing a secondary ion source and further comprising an electrically conducting input tube having an entrance region and an exit region with the entrance region fluidly coupled to the source and the exit region fluidly coupled to the ion trapping region, the ion trapping region comprises a plurality of electrode triads and a plurality of RF quadrupoles. In some embodiments employing a secondary ion source, the apparatus further comprises a laser source positioned to provide laser radiation to the ion trapping region.

In one aspect of the present invention, there is a method of analyzing a sample comprising the steps of creating a flow of gaseous ions or mixture of gaseous ions and gaseous neutral species from the sample, the flow having an axis of flow in a first direction; injecting the flow into an ion mobility assembly, the ion mobility assembly comprising: an ion trapping region comprising a plurality of ion traps to receive the flow; a plurality of parallel mobility tubes, each of the mobility tubes fluidly coupled to at least one of the ion traps; optionally, a plurality of parallel CID tubes, each of the CID tubes fluidly coupled to at least one of the mobility tubes; optionally, a plurality of parallel exit tubes, each of the exit tubes comprising at least one electrode and being fluidly coupled to at least one of the CID tubes or to at least one of the mobility tubes; and, at least one multi-channel RF ion guide fluidly coupled to at least one of the parallel exit tubes, at least one of the CID tubes, or at least one of the mobility tubes; the ion mobility assembly having a separation axis that is orthogonal to the first direction; and, thereafter injecting the flow into at least one TOFMS fluidly coupled to the ion mobility assembly, the TOFMS comprising a position sensitive detector. In some embodiments, the step of creating comprises the step of applying a collimated stream of gas to the flow. In some embodiments, the method further comprises the step of maintaining a pressure of about 0.1 to about 10 Torr in the ion trapping region. In some embodiments, the method further comprises the step of applying a DC electric field to the ion trapping region. In some embodiments, the method further comprises the step of applying an RF voltage to the ion trapping region. In some embodiments, the step of creating further comprises the step of applying an RF voltage to the flow before the step of injecting the flow through the ion mobility assembly, wherein the RF voltage applied to the flow before the step of injecting through the ion mobility assembly is shifted by $\pi/2$ with respect to the RF voltage applied in the ion trapping region. In some embodiments, the method further comprises the step of cooling the flow before the step of injecting the flow through the at least one TOFMS. In some embodiments of the method, the step of cooling comprises cooling with supersonic gas flows. In some embodiments of the method, the step of creating comprises extracting and ionizing gaseous neutral species from a gaseous sample plume. In some embodiments of the method wherein the step of creating comprises extracting and ionizing gaseous neutral species from a gaseous sample plume, the said step of extracting comprises passing a collimated stream of gas through the gaseous sample plume. In some embodiments of the method wherein the step of creating comprises extracting and ionizing gaseous neutral species from a gaseous sample plume, the step of ionizing comprises ionizing with laser radiation. In some embodiments of the method wherein the step of creating comprises extracting and ionizing gaseous neutral species from a gaseous sample plume, the step of ionizing comprises fragmentation of neutral zwitterions. In some embodiments of the method, one or more of the plurality of parallel mobility tubes comprise a front element and the method further comprises the step of applying a constant or variable voltage bias to the front element. In some embodiments of the method, the at least one multi-channel RF ion guide comprises one or more multi-pole RF ion guides. In some embodiments wherein the at least one multi-channel RF ion guide comprises one or more multi-pole RF ion guides, the multi-pole RF ion guides comprises two or more rods and the method further comprises the step of applying a voltage of varying phase and amplitude to the rods. In some embodiments of the method, the step of creating the flow comprises creating droplets with a component selected from the group consisting of an electrospray source, a pneumo-spray source, an atmospheric pressure ionization source, and any combination thereof. In some embodiments of the method comprising the step of creating droplets, the method further comprises the step of splitting the droplets into positively and negatively charged droplets by a quasi-resonant sound frequency field or an ultrasound frequency electric field. In some embodiments of the method comprising the step of creating droplets, the method further comprises the step of drying the droplets by ambient gas heating, microwave absorption, or a combination thereof. In some embodiments of the method comprising the step of creating droplets, the method further comprises the step of applying an electric field to the droplets. In some embodiments of the method, the step of creating the flow comprises creating the flow with a component selected from the group consisting of a laser desorption source, a cluster bombardment source, a secondary ion source, an electrospray ionization source, photoionization source, and any combination thereof. In some embodiments of the method, the method further comprises passing said flow through a differentially pumped low pressure region between the ion mobility assembly and the TOFMS. In some embodiments of the method, the step of injecting the flow through an ion mobility assembly comprises injecting the flow through more than one ion mobility assembly and wherein one or more pairs of the more than one ion mobility assembly are opposed pairs. In some embodiments of the method, the step of injecting the flow through at least one TOFMS comprises injecting the flow into at least one TOFMS comprising a multi-channel detector. In some embodiments of the method, the at least one TOFMS is at least one oTOFMS. In some embodiments, the at least one TOFMS is at least one LoTOFMS. In some embodiments wherein the at least one TOFMS is at least one LoTOFMS, the at least one LoTOFMS is at least one gridless LoTOFMS. In some embodiments of the method, the step of creating comprises creating with a secondary ion source. In some embodiments of the method comprising creating the flow of gaseous ions or mixture of gaseous ions and gaseous neutral species with a secondary ion source, the method further comprises the step of passing the flow through an electrically conducting input tube having an entrance region and an exit region prior to the step of injecting the beams through said ion mobility assembly In some embodiments of the method, the ion trapping region comprises a plurality of electrode triads and a plurality of RF quadrupoles. In some embodiments of the method, the method further comprises the step of post-ionizing neutral species in the ion trapping region with laser radiation.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
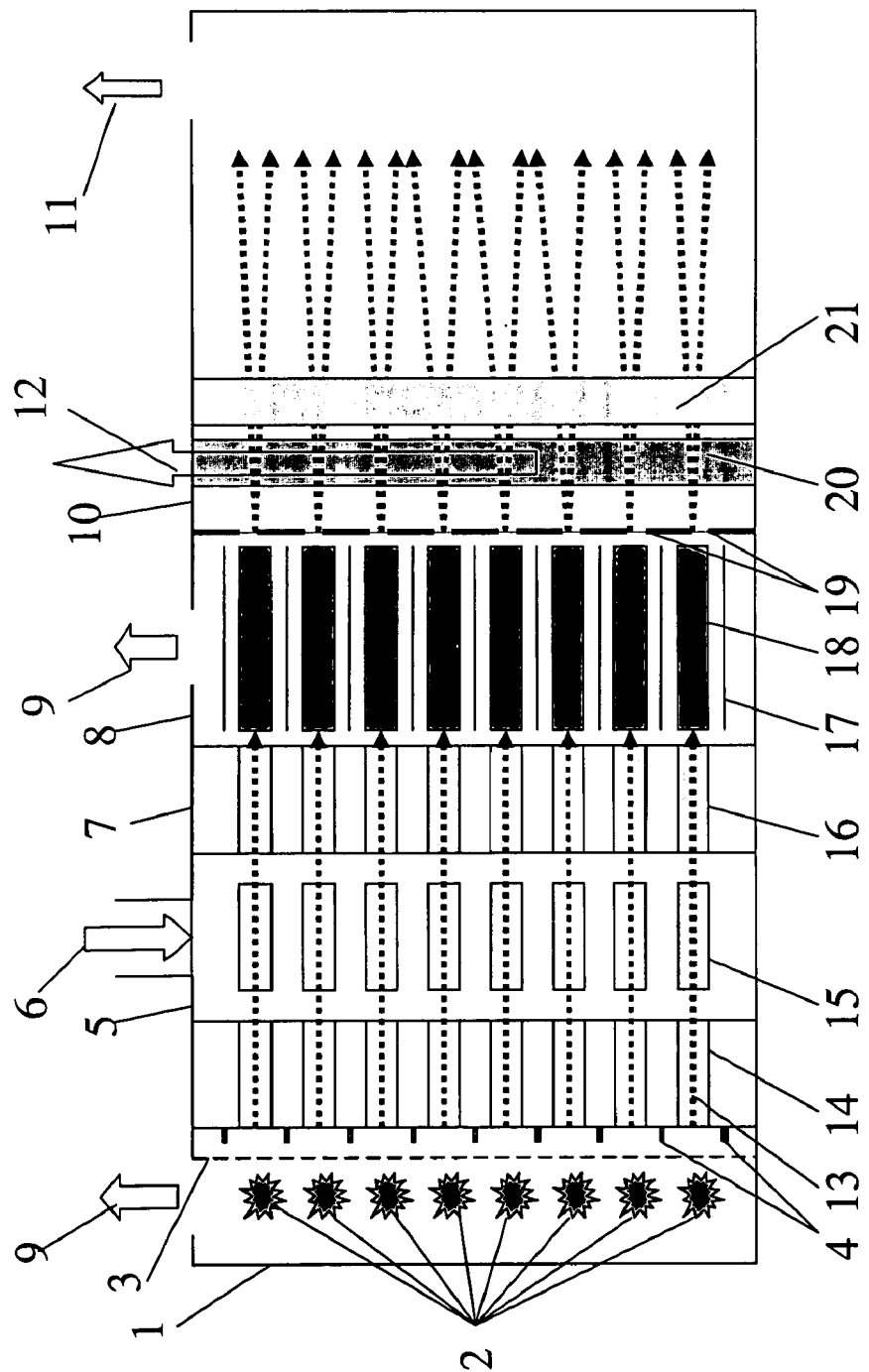
FIG. 1. Schematic diagram of a measuring unit for multi-beam ion mobility drift cell TOFMS with multi-channel data recording, common for most of the embodiments of the invention.

As used herein, "a" or "an" means one or more, unless otherwise expressly indicated or obvious from the context. This is particularly true when reference is made to instrumental apparatuses or individual components of the same.

As used herein, a "plurality" means two or more (i.e., more than one).

As used herein, an "electrode triad" is a distinct group or cluster of three electrodes.

As used herein, a "mobility cell assembly" is defined as a single or multi-channel device which performs mobility separation of ions and comprises a first mobility tube, collision induced dissociation (CID) tubes wherein collision-induced ionization occurs, and final ion transport with cooling gas flow through "exit tubes" into multi-channel RF-ion guide. In the multi-channel embodiment, the mobility cell assembly comprises a plurality of first mobility tubes, CID tubes, exit tubes and RF-ion guides, preferably with each of the aforementioned component in series with one another and each series in parallel with at least one other series.

As used herein, "mobility tube" is an ion mobility cell or other cell for the transport of ions; the terms ion mobility cell and mobility tube are synonymous herein.

As used herein "collision induced dissociation tube" or "CID tube" is a tube in which high electric fields may be created sufficient to provide collision-induced dissociation of ions. In the present invention, the CID tube, when present can be used for collision-induced dissociation or alternatively, the collision-induced dissociation mode may be disabled and the CID tube may be used for cooling such as gas cooling and/or RF cooling.

As used herein "exit tube" is a tube with a diameter less than a preceding tube to which it is fluidly coupled, said exit tube being used as a gas collimating and ion transport tube.

As used herein, the term "separation axis" as it relates to an ion mobility assembly or any individual component of an ion mobility assembly is the axis defining the direction of travel of ions and/or neutral species traversing or being transported through the ion mobility assembly or any individual component of the ion mobility assembly.

As used herein, a "ion trapping region" or "trapping region" is part of the entrance interface between the ion source and the mobility cell where ions preferably of both signs and possibly neutrals are accumulated. Neutrals are ionized and the resulting ions are trapped in multiple traps before penetrating a mobility cell.

As used herein, an "orthogonal collection region" is defined by the volume between at least one electrode and/or voltage grid pair through which ions (possibly of both signs) and neutrals which are mixed with a carrier gas pass orthogonally in front of the entrance of at least one IM tube. Neutrals which are formed within the gas flow through this region are transformed into ions by an ionization or fragmentation process (such as by a laser) within this region.

As used herein, "MALDI" means matrix assisted laser desorption ionization.

As used herein, "SIMS" means secondary ion mass spectrometry.

As used herein, "FAB" means fast atom bombardment mass spectrometry.

As used herein, the term "TOFMS" is defined as a time-of-flight mass spectrometer including both the linear or reflectron type; as used herein, "oTOFMS" is defined as a time-of-flight mass spectrometer both linear or reflectron type configured orthogonally to the analytical axis of a preceding instrumental platform such as, for example, the separation axis of an ion mobility cell; "LoTOFMS" is specifically defined as a linear oTOFMS. The oTOFMS and the LoTOFMS are examples of a TOFMS.

As used herein IM-oTOFMS refers to a combination of an Ion mobility spectrometer with an orthogonal time of flight mass spectrometer.

In applications which use ion mobility cells filled with a few Torr of buffer gas as a volume/charge separation stage in front of a mass spectrometer, the cooled ions exit through a small aperture into a differentially pumped low pressure region before the high vacuum region of the mass spectrometer. To minimize transmission losses through the small aperture, the ion beam inside the mobility cell should be focused. Ion beams should be as narrow and parallel as possible in the region between the mobility cell and TOFMS to allow the use of small differential pumping apertures (enabling lower gas flow) and to achieve higher mass resolution for TOFMS operation. Therefore the beam should be cooled as much as possible to obtain low divergence. If this divergence is small in directions orthogonal to the direction of the initial ion beam, then multiple ion beams may be kept isolated all the way from the ion source to the multichannel detector plane in the TOFMS in order to increase the instrument throughput (proportional to the number of ion beams). Such an approach is feasible because: (i) devices for multi-channel data recording (multi-channel time-to-digital converter ("TDC")) are available and widely used; (ii) it is possible to transport ions inside small tubes without losses by coating conducting surfaces with thin dielectric films as described in details below; (iii) it is possible to organize mobility separation of ions in a gas counter-flow in a controllable time scale so that the use of different channels of TDC for position sensitive detection may be used for recording of plurality of ion beams; (iv) gas flow through narrow tubes from high pressure to vacuum can have divergence corresponding to a gas temperature of 1° K or less; and (v) ions hundreds of times heavier than gas atoms and traveling in such a gas flow may have a divergence corresponding to about 10° K temperature.

In the present invention, a multichannel IM-oTOFMS detection unit (400) shown schematically in FIG. 1 and comprises a ion mobility assembly (comprising multi-channel ion mobility drift cells) coupled to a oTOFMS (124) with multi-channel data recording is used for different embodiments for analysis of ions of both signs which are intimately mixed with a gas flow (66). These ions may be directly produced by known ion sources such as MALDI and ESI and are subsequently combined within a gas flow (66) in which they are transported into an ion trapping region (1) where they can be further localized within multiple RF traps (2). The ion traps n the ion trapping region may also be DC field traps. In some embodiments ions may be injected into detection unit (400) as shown in FIG. 1 by a gas flow (66) which spreads the entrained ions across the front element (40) of each the ion mobility tubes. Alternatively some embodiments will bring multiple source of ions simultaneously into the trapping region (1) of unit (400) by a motion along axes into the FIG. 1 which bring each ions from each ion source into specific registry with one of the multiple mobility channels. Ions may also be created within this region (1) by post-ionization of any neutral analyte which has been also entrained in the gas flow (66) along with the directly produced ions. The preferred means for post-ionization of neutrals is laser irradiation of the flow or plume containing the neutrals, however other means, such as, but not limited to, electron attachment, chemical ionization, use of a metastable atom beam, helium ion Auger neutralization, and other means known to those of skill in the art are applicable. Whatever the method of introduction of the ion laden gas flow (66) the ions are accumulated in the trapping region (1) in separate RF traps (2) so that individual ion beams (13) can ultimately be formed and transported through an multi-channel IM drift cells. The direction of travel through the IM drift cells and the remainder of the ion mobility assembly defines the separation axis of the ion mobility assembly. Depending on the shape and mass of the ions some pre-selection between different traps may be achieved during the filling process. To provide favorable conditions for RF ion trapping, the gas pressure inside the trapping region is maintained at the level between a few Torr and a few tenths of Torr by appropriate pumping (9). After ion accumulation in the RF trapping region (1), DC biases are applied to grid (3) to move ions to quasi-stationary new locations next to the entrance element (40) of the corresponding first mobility tube (14) and the ion are localized there by a combination of a part of the gas flow (6) emanating ultimately through the front element (40) of the IM tube (14) (element (40) may at this time have close to zero electric field across it) and by the electric field provided by collimating electrodes (4) and grid (3). The front element (40) may simply be several electrodes of the IM tube (14) which can controllably biased alternatively to near or below zero while ions are being accumulated in the trapping region and then to some attractive potential which initiates the ion flow (13) through the IM tube (14). Alternatively the front element may be a discrete section of capillaries or may even be a microchannel plate section which is fluidly coupled to the front end of each IM tube (14). Preferably, the surface around the entrance of one or more of the mobility tubes (14) and the front element (40) may be coated with thin dielectric or piezoelectric thin films and charged before the experiment by charges of the same sign as the ions which are being trapped. Ions located around the corresponding entrance are inserted into individual IM tubes (14) by rapidly changing the field on the front element (40) and inside the mobility tube (14) from zero to a value which will begin the transport of the ions from region (1) to their ultimate analysis in the oTOFMS (124). Trapped ions thus start their motion (13) against the gas flow so that smaller ions with large mobility move most quickly. To prevent an influence of different electrodes voltages on the traps (2) a certain DC voltage, sometimes, mixed with RF voltage, is applied to the screening grid (3) throughout ion accumulation. Once trapped ions have been introduced into the IM analyzer assembly the RF trapping region (1) can be re-activated and the trapping of ions from the continuous incoming flow (66) resumed. After emerging from the mobility entrance section (14), ions travel to the middle region of the ion mobility cell (5) where gas flow (6) is inserted and the pressure is maintained constant. This pressure may be between 1 and several tens of Torr. Most commonly the gas will be helium, although other gases or gas mixtures may be used. CID can be performed in the region (5) between IM tubes (14) and/or between IM tube (14) and exit tube (16). While the figure shows gaps in this region it should be emphasized that this entire assembly can be continuous and the CID produced by local biasing of discrete elements within one continuous assembly. It is equally possible to build these as discrete elements. Accordingly, throughout this document and including the claims, where a reference may be made to a number of discrete elements (e.g., a mobility tube, a CID tube, an exit tube, etc.), it should be understood that this encompasses these elements as discrete elements or as part of one continuous assembly. Thus, extending the previous example, one tube may comprise a mobility section, a CID section, an exit section, or any combination thereof. The usual function of the discrete components or sections of a continuous assembly is to collect ions coming from a preceding discrete component or section such as a mobility tube (which may be a first mobility tube) and transport them to a succeeding discrete component or section of a continuous assembly, which may be an exit tube (16) as shown in FIG. 1 (see also FIG. 12 for a vertical cross-section of this region of FIG. 1).

It should be noted that the instrument of FIG. 1 could optionally comprise an orthogonal collection region located upstream of the ion trapping region. The orthogonal collection region would comprise a volume between at least one electrode and/or grid pair through which ions (possibly of both signs) and neutrals which are mixed with a carrier gas pass orthogonally in front of the entrance of at least one IM tube. Neutrals which are formed within the gas flow through this region may be transformed into ions by an ionization or fragmentation process (such as by a laser) within this region. With reference to FIG. 1, the orthogonal collection region would be located to the left of ion trapping region (1). In such cases, as ions and neutrals travel in the flow (66), they enter the orthogonal collection region and are accumulated by the manipulation of the voltages on the voltage grids and or electrodes. By intermittently applying voltages on grids and/or electrodes, it is possible to create a field which moves ions orthogonal to the direction of ion/gas flow motion and into the ion trapping region, thereby providing control of the filling of the ion trapping region.

The ions may be transported to one or more intervening mobility tubes in series with an exit tube. At certain time intervals high electric field may be created inside or between sections to provide CID (collision induced dissociation) of specific ions. Alternatively, the front section of the exit tube element (16) can either be used for CID or can be used for cooling applications without collision induced dissociation. After passing through the middle region of mobility cell (5) ions penetrate the region of exit tubes (7). The exit tube (16) diameter is less than the preceding tube (15) to which it is fluidly coupled and is used as a gas collimating tube. The mobility carrier gas flows through each exit tube (16) along with mobility separated ions. The exit tubes (16) must also have electrodes for creating electric fields which will move ions since the gas flow at the beginning of these tubes is relatively slow. By choosing and controlling the pressures in region (7) and region (8) it is possible to create a highly directed gas beam which emerges from the exit tubes into vacuum with low divergence (corresponding to the absolute temperature of about 1K or lower). Ions moving with gas in these tubes are only partially cooled since they do not have quite enough time to come close to equilibrium with the helium gas flow, so their divergence is somewhat higher. It is at this point that a multi-channel RF-ion guide (8) is used to focus and cool each ion beam (123) so that the ions attain the velocity close to that of cooled IM buffer gas beam (Helium in the example). This ion guide (8) comprises multiple pairs of rods (18) (in the horizontal plane) each pair of which is separated by confining plates (17) (in the vertical plane). RF-voltage of the same phase is applied to the rods (18). Confining plates (17) have the same voltage as oTOFMS (10). These plates provide focusing of ions between rods of each pair. This apparatus provides low divergent ion beams which may be inserted through small orifices (19) directly into an oTOFMS or alternatively (as shown in FIG. 1) into a differential pumping region (127) containing special ion mirrors (20, 21).

Figure 12:
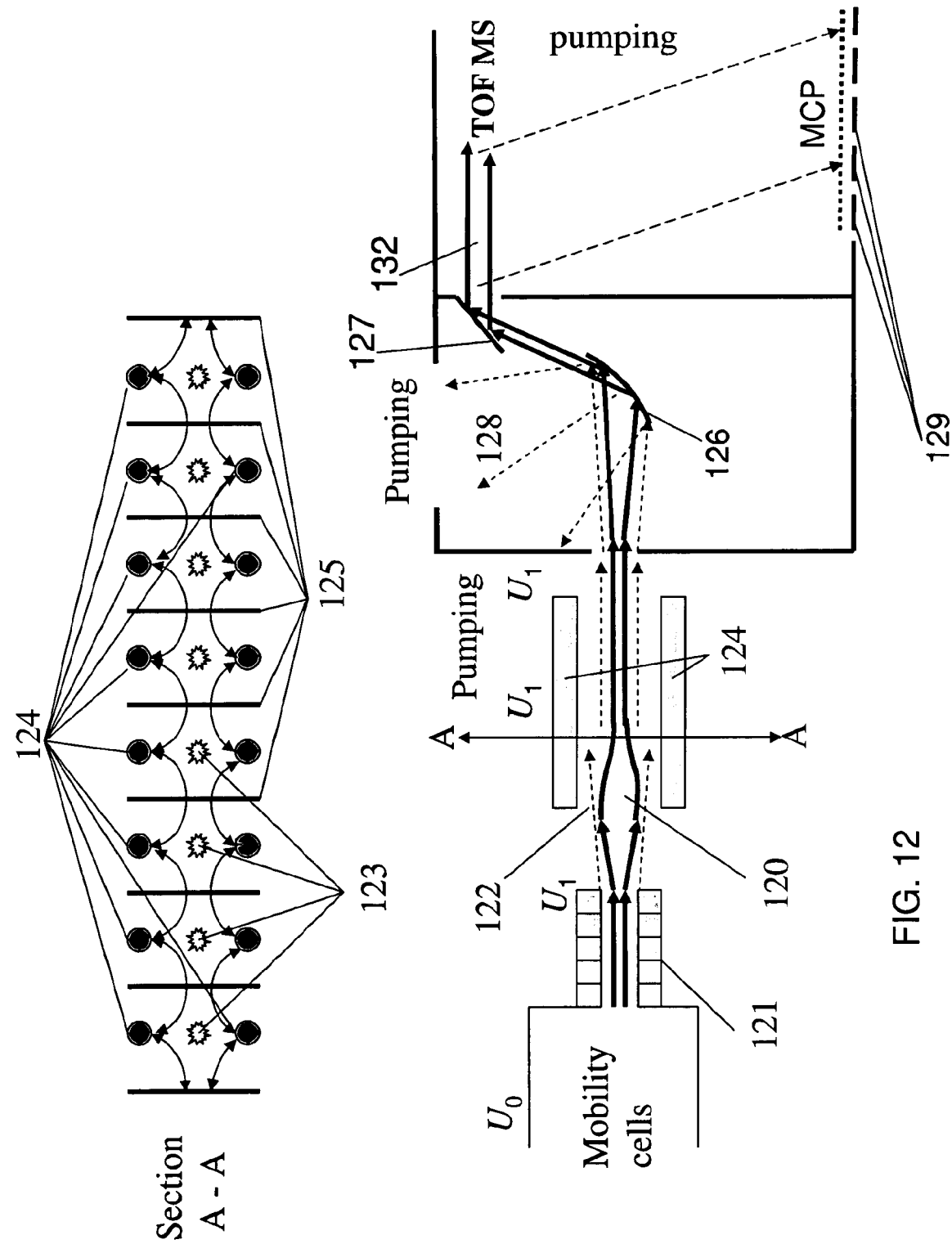
FIG. 12. Schematic view of the interface used to introduce separate ion beams into TOFMS.

Reference to FIG. 12 and FIG. 1 show that the ion beam may be made even more nearly parallel by two reflections from ion mirrors (20, 21) constructed from thin film coated conductors. Both mirrors (20, 21) are made of a conductor coated by a thin charged dielectric film. Alternatively the mirror may be made of thin metallic strips (a few micron-wide separated by a few micron) each strip of which is biased alternatively with a fixed positive and negative voltage or even an RF voltage. This assembly may be optionally covered with a thin dielectric film. Alternatively piezoelectric thin film with thin alternating electrodes which can be controllably biased with DC or RF voltages may be used. The reflection sequence of the cooled ion beam from the mirror can be best understood by first reference to FIG. 12 (which is a vertical cross-section of FIG. 1) and then referring back to FIG. 1. The first reflection of the ion beams are from parabolic mirrors such a cylindrical parabolic mirrors (20) and the second reflection is from flat mirrors (21). The focus line of the parabolic mirror crosses the input orifices (19) so that, after reflection in the vertical plane, the diverging ion beams (123) become nearly parallel. This nearly parallel beam (135) is then reflected from the second mirror (21) (flat) so that the ions cross the second set of apertures (121) and enter the oTOFMS (124). By contrast, the IM buffer gas flow (128) is reflected diffusely from the parabolic mirror (20) and is efficiently pumped (12). Thus only moderate pumping speeds (11) is needed to provide sufficient vacuum in the TOFMS analyzer. This is a further advantage of this invention and contrasts to prior art designs relying on skimmer cones which are co-axial to the ion and gas flow paths. In FIG. 1, a series of eight parallel channels are shown; however, this can vary from one series to any number of series greater than one. Alternatively the reflection of the diverging cooled ion beam (123) could be done with only one cylindrical parabolic mirror so that the beam would exit the differential pumping region (127) at some angle (such as 90 degrees) relative to the axis of the axis of the RF cooling assembly. The oTOFMS would then be oriented to receive the cooled parallel ion beam after only one reflection. An alternative embodiment which is slightly more difficult to manufacture would to have a parabolic mirror (127) instead of a cylindrical parabolic shape. This would focus the diverging cooled beam (123) into a parallel beam with a round cross-section.

Figure 2:
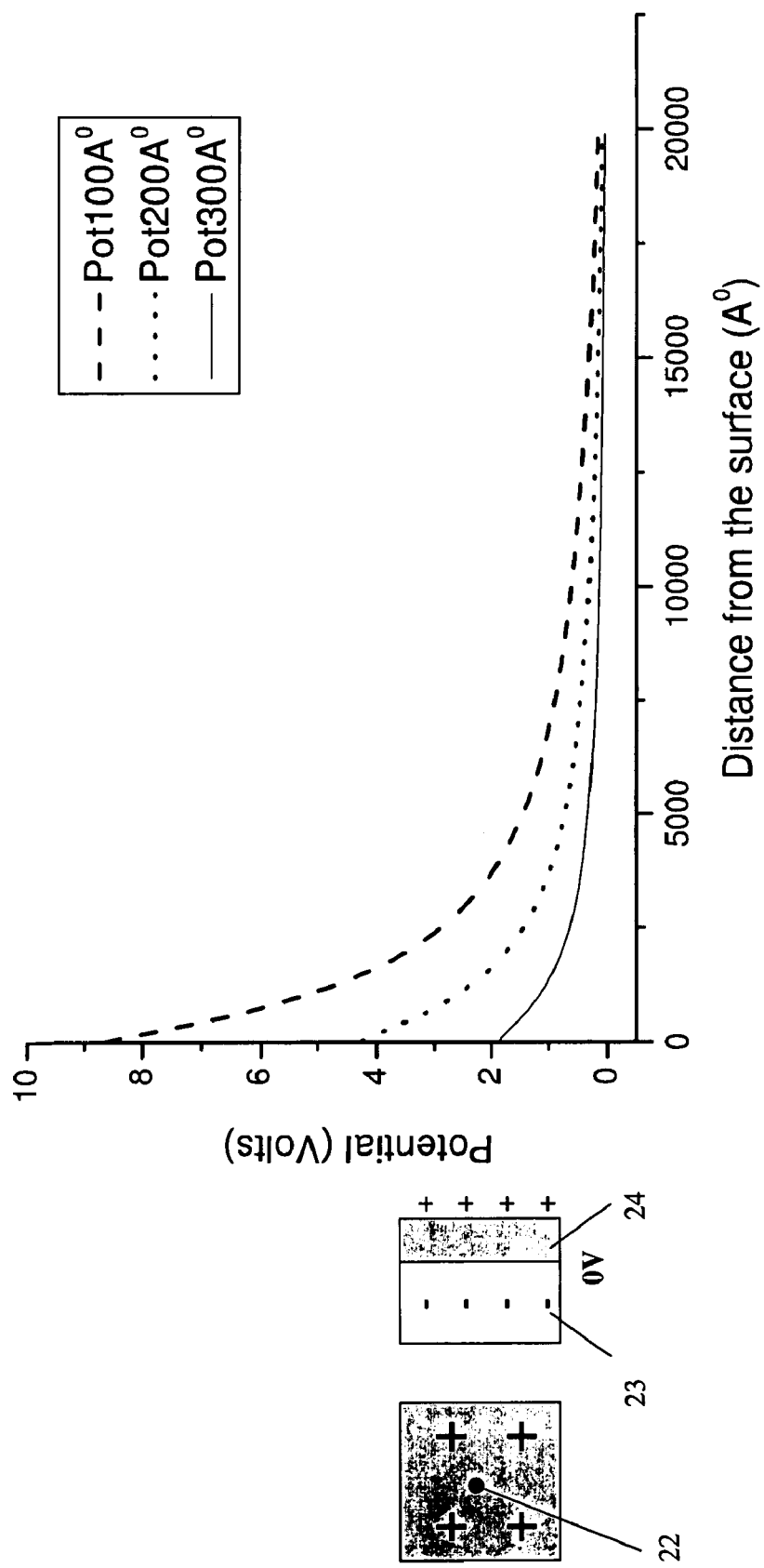
FIG. 2. Minimal potential difference in space near a conductor coated with a 1000 Å thick dielectric film on which are placed uniformly distributed surface charges. Computer simulations of the potential from three structures with different minimal distances between the charges are shown.

In the preferred embodiment of the present invention, charged thin film coatings of conducting surfaces are used to increase the mobility cell ion transmission. This coating was described in U.S. Pat. No. 6,992,284 to Schultz, et. al. where the coating is used to increase the mobility cell ion transmission. The result of computer calculation of potential distribution near such coated surface is shown in FIG. 2. Assuming a uniform distribution of positive charges on the surface of 1000 Å thick dielectric film (24), the point for potential calculation is chosen between the charges (22). It is shown that for each positive charge on the surface the corresponding virtual "mirror" negative charge is formed inside the conductor (23) at the distance from the conductor surface equal to the thickness of the film. The set of dipoles on the surface is formed and potentials of their electric fields for the minimal distances between positive charges of 100 Å, 200 Å and 300 Å are shown. If ions moving in gas have the energy in the direction orthogonal to the surface, which is lower than the calculated potential of the surface, ions cannot reach the surface and are reflected back. Taking into account the permittivity of the dielectric reduces the potential values proportionally to the value of permittivity.

Figure 3:
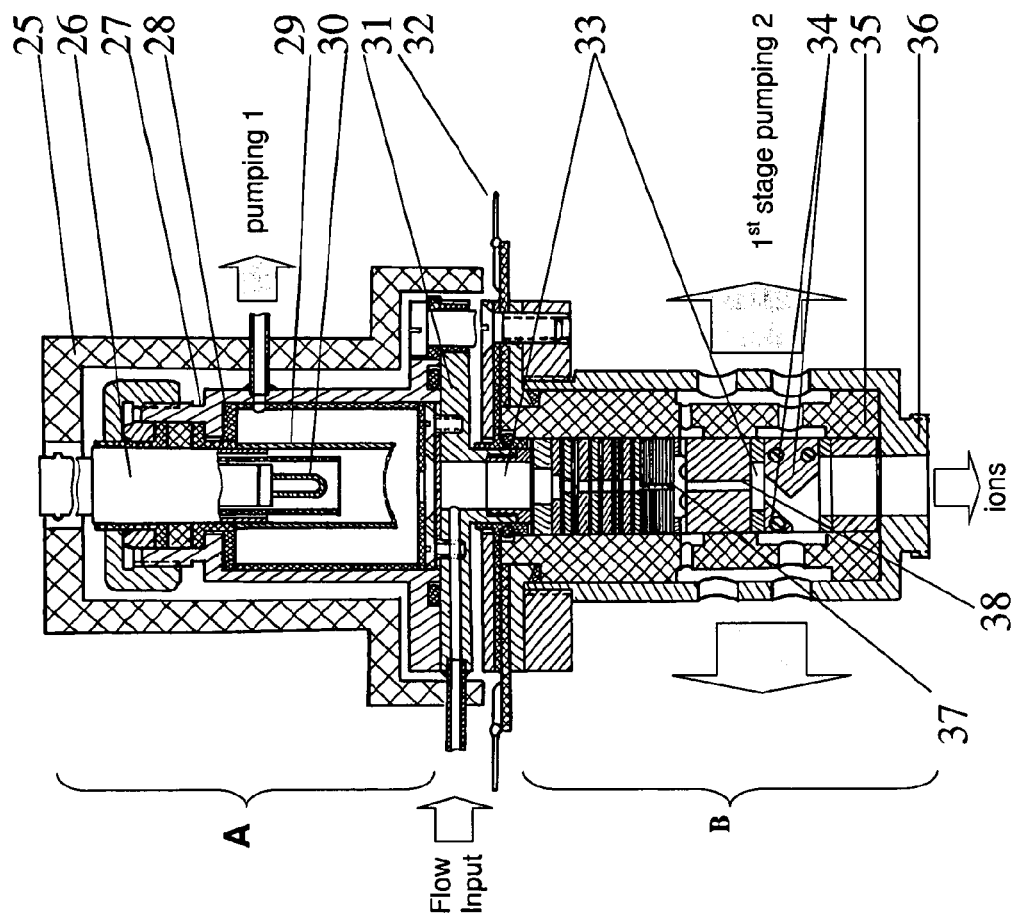
FIG. 3. Drawing of the experimental setup used to test the ion cooling process in a well-collimated flow of helium. All internal surfaces parallel to the gas flow are coated by thin dielectric film and charged by the glow discharge before the measurements.

In another embodiment of the present invention, there is a significant cooling of gas emerging from the tube connecting regions of differential pressures. Corresponding measurements were performed using experimental setup which is shown in FIG. 3. Two parts of the setup are shown here: A, ion source and B, ion interface assembly. Outer poly-foam jacket (25) confines the glow discharge ion source. The following parts of the source are shown: high voltage lead (26), stainless steal housing (27), inner Teflon insertion (28), outer HV electrode (29) and inner HV electrode (30). The ion interface assembly comprises following parts: entry electrode of the interface (31), voltage leads of electrodes (32), focusing electrode assembly (33), ion mirror with dielectric coating (34), centering Teflon bushing (35), and interface housing (36). Helium ions mixed with hexabromobenzene ($C_6Br_6$) ions from the ion source, A, come to the sectioned tube (37) with electric field inside. This tube (0.7 mm in diameter and about 5 mm long) has high pressure (several Torr) at the inlet and about 10000 times lower gas pressure at the outlet. The tube is coated inside with dielectric film. Ions cooled by the gas flow enter a larger (1.5 mm in diameter, 1 cm long) field-free tube, which is also coated with dielectric film. The ion mirror, formed by two plates (34) and coated with charged dielectric film, prevents narrow gas flow from going directly into the detection section. Ions only have some parallel displacement of their trajectories due to mirror reflection, but the helium flow has diffusion reflection and the main part of the flow is pumped away by the first stage pumping. Further downstream (about 14 cm from the interface) ions go through a sliding slit, and finally reach a secondary multiplier and are counted by an ion counter.

Figure 4:
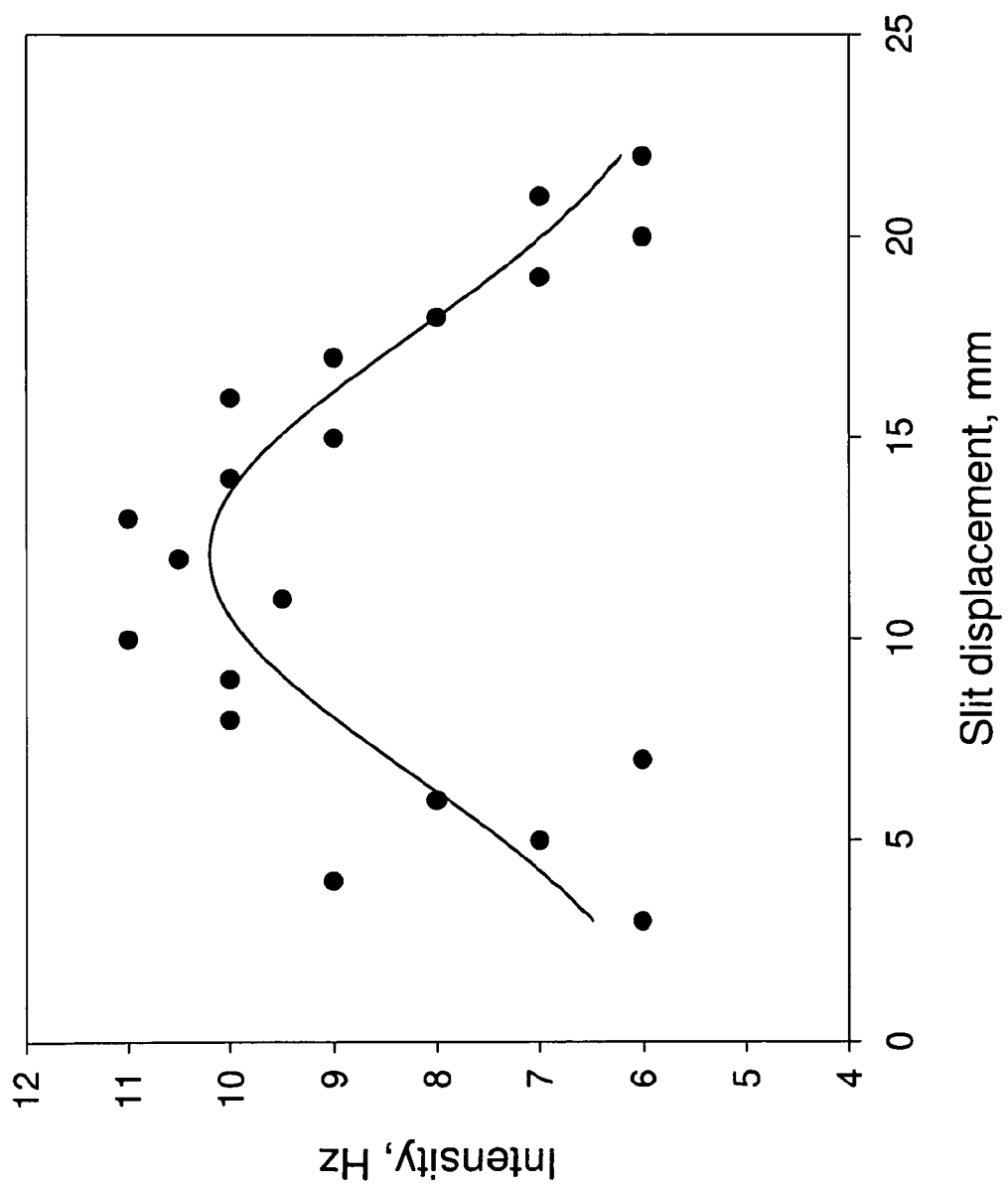
FIG. 4. Distribution of helium ion beam experimentally measured using the setup shown in FIG. 3. Intensity through a sliding slit is measured. This distribution corresponds to the helium flow temperature of ~1K implying that helium ions are in equilibrium with gas flow.

FIG. 4 shows the result of measurements using pure helium in the ion source. Round symbols represent experimental data. The solid line is a simulated Gaussian distribution corresponding to the ion beam average angular divergence of 0.046 rad. equivalent to an ion temperature of ~1K. Since the charge exchange between helium ions and atoms is a resonant process with high cross-section, it is highly probable that helium ions and atoms are in thermodynamic equilibrium in the flow. Therefore, 1K is the estimation for the helium atom temperature as well. This is a lower limit estimation since helium ions must come through the two plate ion mirror which is not ideal and may contribute to additional divergence of the ions. It is also possible that some portion of ions inside this mirror may give their charge to helium atoms which are then reflected in random directions from the mirror plates which increases the ion divergence. Theoretical estimation of the gas temperature is about 0.3K.

Figure 5:
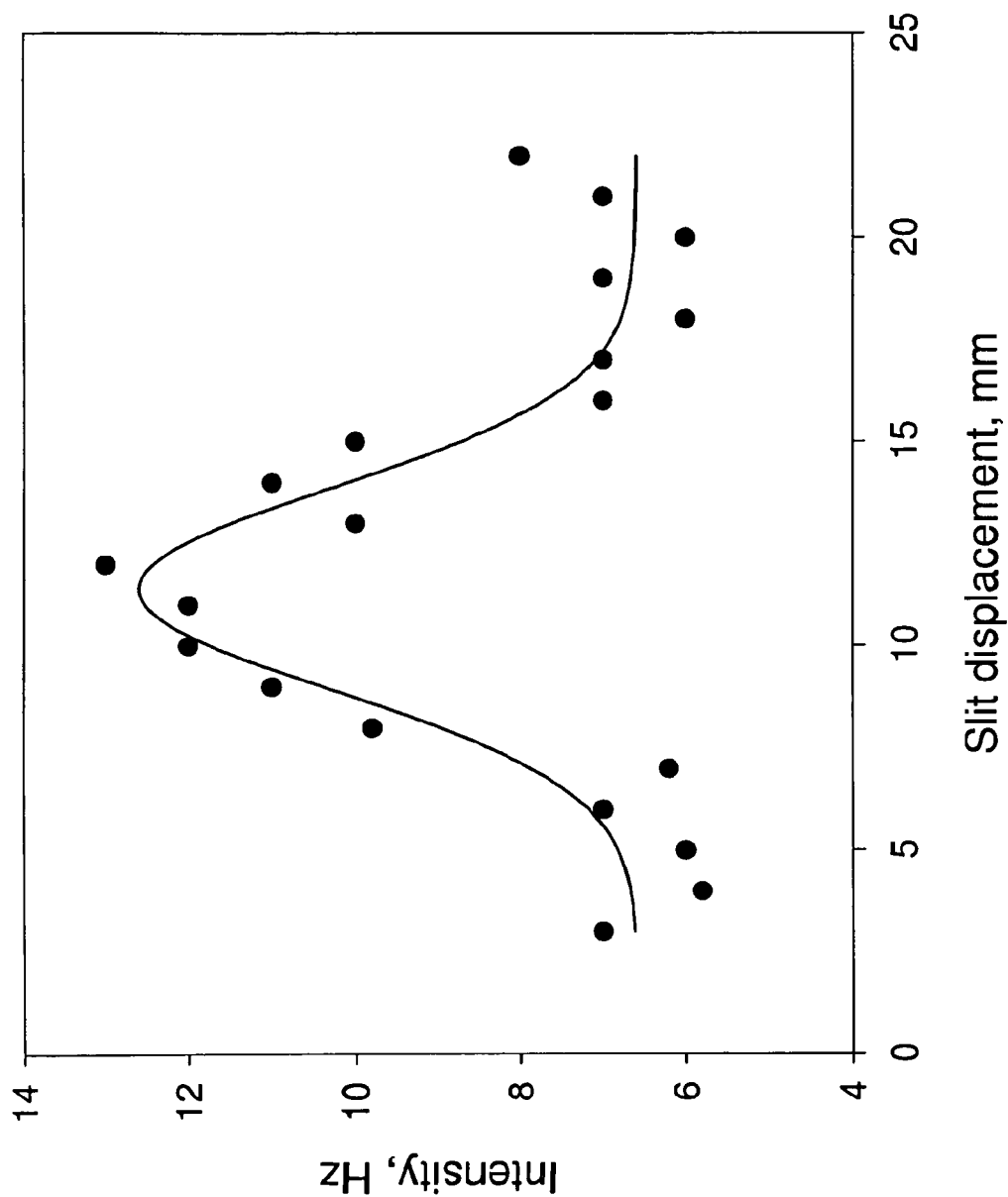
FIG. 5. Distribution of $C_6Br_6^+$ ions, corresponding to 10-20K temperature range.

Data shown in FIG. 5 is for the C6Br6/helium ion mixture. The average ion beam angular divergence is about 0.021 rad. Thus, the upper estimation of the ion temperature is about 10 to 20K. The upper estimation is achieved for ion drift velocity being equal to the gas drift velocity ~1400 m/sec. The lower estimation corresponds to the ion drift velocity ~1000 m/sec. It is interesting to note that computer simulations predicted an angular divergence about two times higher than the measured value for this type of ions. This could be explained by the use of a rigid model for ion-atom collisions in computer simulations. We assume that after collision with ions the gas atoms travel in random (and uniformly distributed) directions in the center of mass reference system both in case of an elastic collision and a breakdown of a previously formed ion-atom complex. This model may be valid for ions moving in "stationary" gas, but is not suitable for ions moving inside the gas flow where atoms have a preferred direction of motion. When gas and ion temperatures decrease, the formation of ion-atom complexes becomes more probable and their lifetime may be longer than the time between consecutive collisions. Therefore, the next collision may destroy the complex and the probable direction of ejection of the atom involved in the complex formation should be opposite to the impact direction of the new atom. In this case the relaxation of the kinetic energy of ion may take place almost independently for the direction of the main motion of ions and the gas flow, and for the motion in orthogonal directions. Therefore, the divergence of ions may be significantly lower than that predicted by the ion-atom collision model used in the simulations. The main conclusions from the experimental data are: a) coating of electrodes by thin dielectric film which, when charged, provides reflection of ions moving in a gas with relatively low energies; b) helium atoms going through tubes from relatively high to low pressure regions may be cooled significantly—close to or below 1K,—and ions moving with this flow may be cooled in a direction orthogonal to the flow, probably to the level of a few degrees K.

Figure 6:
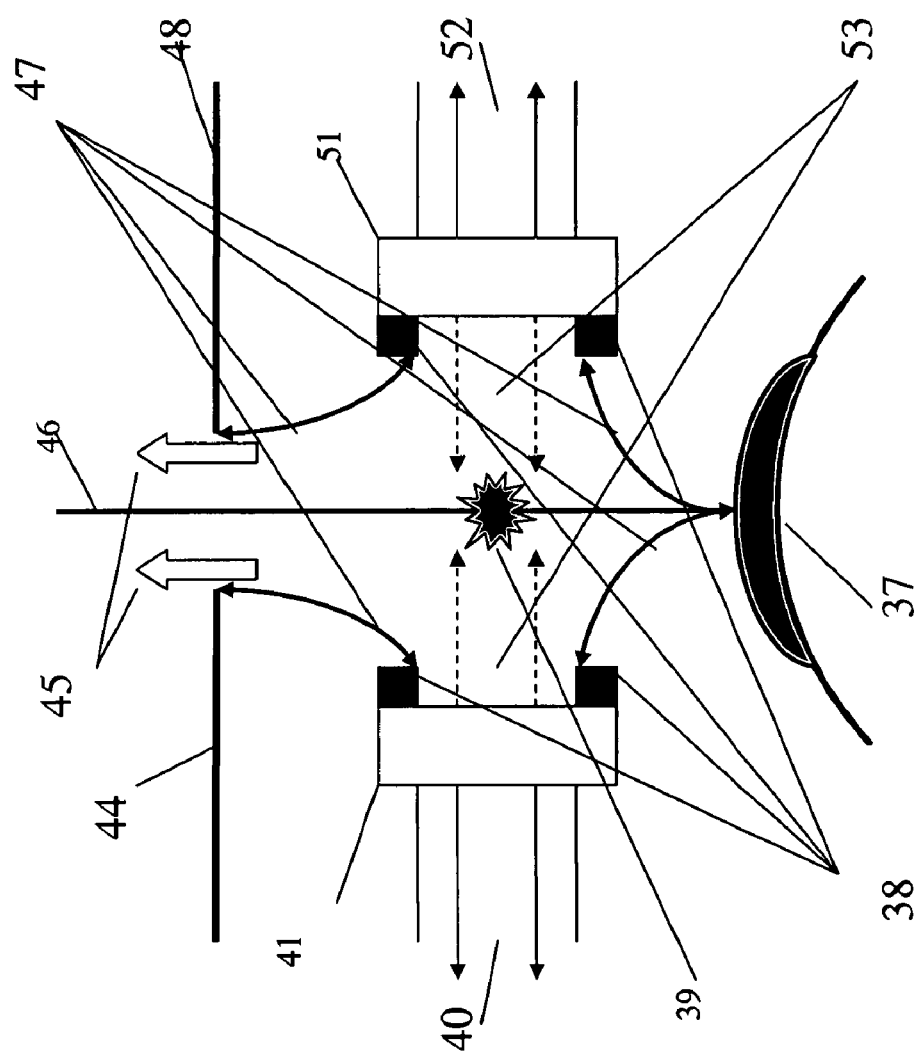
FIG. 6. Schematic diagram of a multi-beam MALDI ion source with extraction and trapping of both sign ions using an RF-field and a gas flow for tissue imaging.
Figure 7:
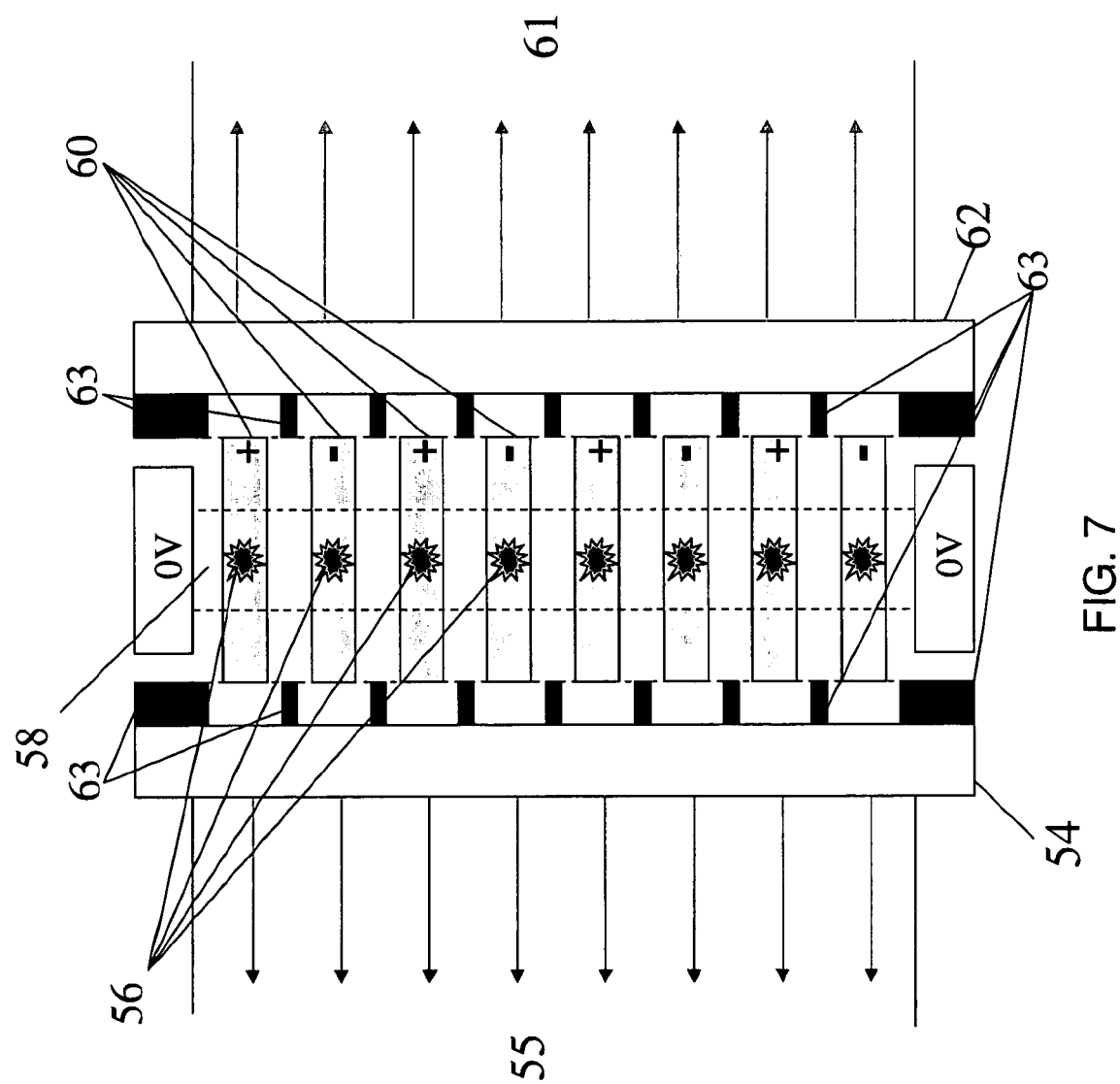
FIG. 7. Top view of FIG. 6. After RF accumulation is suspended positive ions are inserted to the left, negative ions—to the right.

One embodiment of the present invention enables extraction of ions of both signs from several spots on a MALDI sample. This is shown in FIG. 6 and FIG. 7, (which is the top view of FIG. 6). This embodiment is motivated by the fact that extracting ions of only one sign enriches the sample surface with ions of the opposite sign so that continuous electrostatic extraction of the desired ions becomes more and more difficult. Ions may lose their initial charge and may also change their conformation. It is better to extract both types of ions at once even if only one type of ions is detected. A sample (65) is located on a curved (cylindrical) surface (37) irradiated by several laser beams (46), This sample (65) might be for example, a biological tissue slice into which a MALDI matrix has been intermixed; however, any flexible polymer could also be analyzed. Above this sample are located two multichannel IM-oTOFMS measuring units (400) in an opposed configuration with respect to one another and are fluidly coupled between the sample electrode (37) and RF electrode (48). "Opposed" in this sense includes, for example, "vertically opposed", "horizontally opposed", "diagonally opposed", etc.; all that is required is that the opposing measuring units are configured 180° with respect to one another. The RF trapping region (1) as in FIG. 1 is defined by the surface electrode (37), the top RF electrode (48) and by the collimating electrodes (4) two each on each IM entrance element (40) on two opposed units (400) one of which is biased to transmit negative ions and the other of which is biased to transmit and detect positive ions. An RF-field (47) created between this surface electrode (37) and the collimating electrodes of the mobility cells (4) extracts ions of both signs from the MALDI plume. It is necessary to use a convex sample plate to effectively extract ions of moderate size. For large ions the effect of the gas flow (45) may become more important as the effective RF-field force on the ions decreases with the ion mass. Ions of both signs arise into to the region where the RF-field is close to zero (2) and are trapped there. A DC-field with field lines from left to right is applied between the two opposed entrance elements (40) of the mobility tubes. This bias shifts the positive ions to the left mobility cell and negative ions to the right. Therefore, ions of different sign have less probability to recombine during accumulation in traps. In addition to the RF-field, the gas flows (89) from the mobility cells entrance (40) provide ion trapping in the vicinity of the mobility cells. To trap ions from different spots on the MALDI target in different traps, the cylindrical MALDI target electrode (37) and the top repeller electrodes (48) are both divided into strips (shown in FIG. 7 (60)) where RF voltages with alternating phases are applied. Potentials of the collimating electrodes (4) and the mobility tubes entrance element (40) are DC. After having accumulated ions in traps (2) (see FIG. 7), the DC field between the entrance elements (40) on the mobility tubes is further increased to overcome trapping force of RF-field (47) and gas flows (89). Ions reach the IM drift cell entrance elements (40), which may be coated with a thin film and are trapped around orifices of the mobility tubes by the combined actions of the electric field between collimating electrodes and mobility tubes and the counter flow of gas from the tubes. Next, a new accumulation period starts. At the same time ions localized at the entrance elements (40) of the mobility cells are inserted into the tubes (14) by gradually increasing the electric fields inside the tubes and across element (40). Positive ions (41) go to the left measuring unit (400) and the negative ions (52) to the right (400). The following details are also shown in FIG. 7: pairs of opposing multichannel IM-oTOFMS measuring units (400), positive ion flow (41), trapped ions (2), a slit for pumping (58), the strips with alternating RF-voltage (60), and negative ion flow (52).

Figure 8:
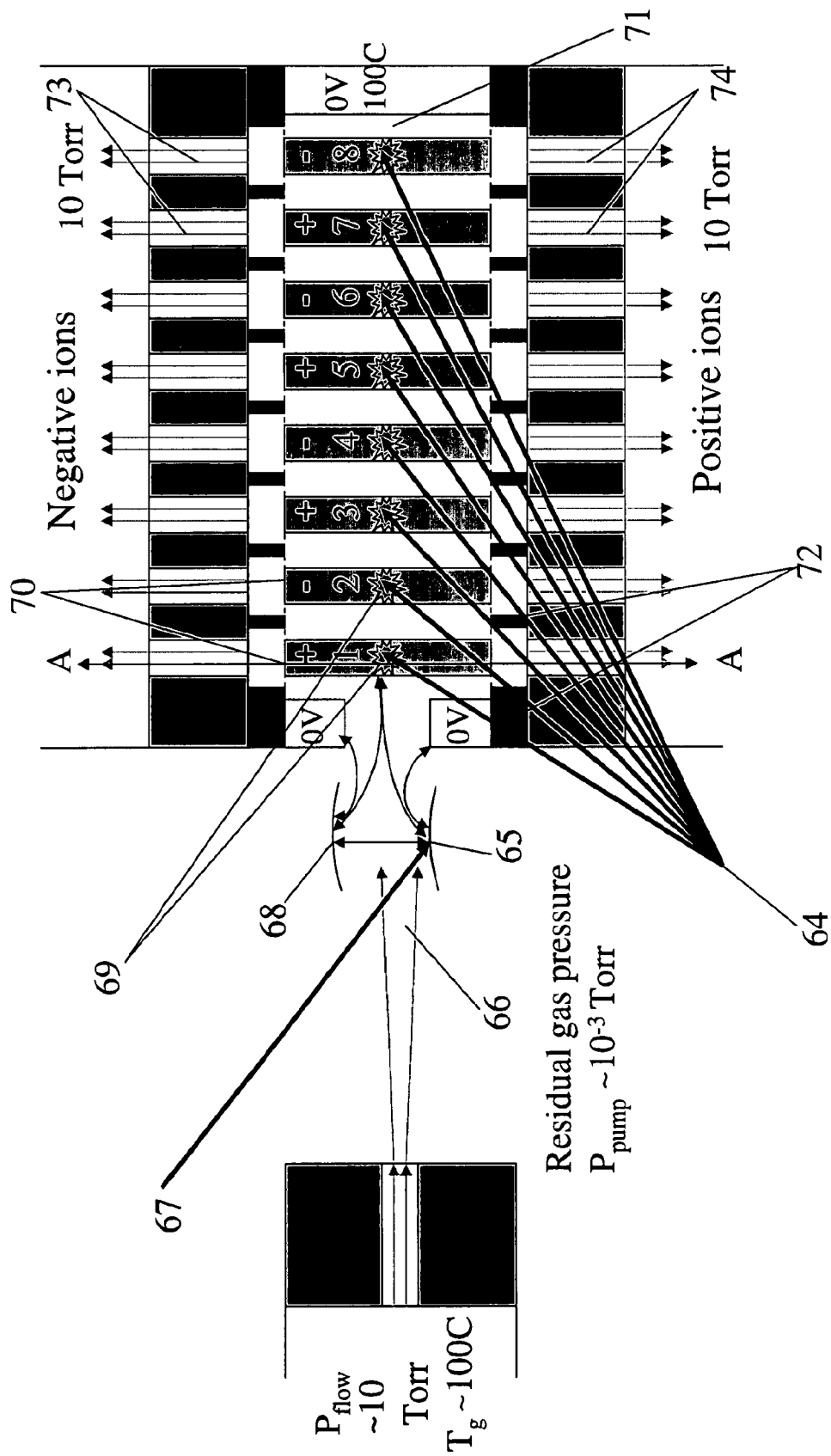
FIG. 8. Schematic diagram of a multi-beam MALDI ion source showing extraction and trapping of ions of both signs as well as neutrals by the combined effects of RF-fields and a well collimated gas flow followed by post-ionization of neutrals.
Figure 9:
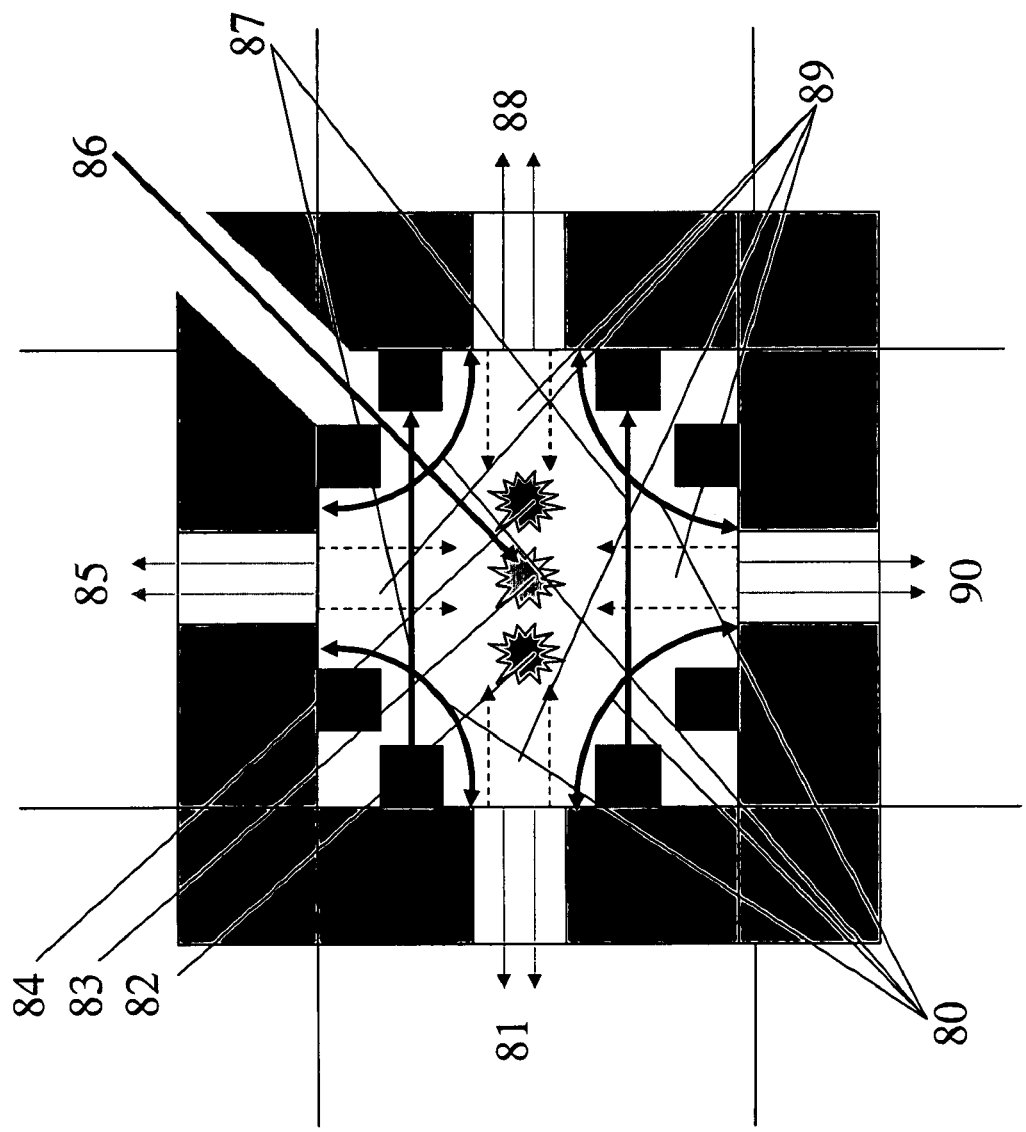
FIG. 9. Section A-A of FIG. 8. Trapped neutrals are shown in the center, negative ions from the MALDI target on the left, and positive ions on the right. After inserting accumulated ions into left and right measuring units, neutrals are ionized. Positive ions from neutrals after their ionization go to the top measuring unit, negative ions—to the bottom one.

Another way to maximize sample use is to collect neutrals from the sample plume and generate ions in addition to the ions initially formed in the MALDI plume. This is illustrated in FIG. 8 and FIG. 9. For the effective extraction of neutrals from the MALDI plume produced by the laser beam (46) from the target (65) (which may be a solid surface, a gas volume or a liquid surface), a collimated gas flow such as a helium flow (or of another gas or mixture of gases) (66) is used. The initial gas temperature is maintained at about 100° C. to increase the gas flow velocity and thus provide some heating of the species coming from the MALDI plume. Ions of both signs from the MALDI plume are also subjected to RF-field extraction force by applying an RF-voltage (67) between the MALDI target plane (65) and an opposite electrode (68). The phase of this voltage is shifted by $\pi/2$ compared to that of RF-voltages applied in the trapping region (1) between sets of mobility tubes. The RF-field (64) is thus decreased from the region of the target to the locations of traps (2) but there is no zero-field in any point of ion motion up to the location of the first ion trap (2). As a result, no ions are trapped on their way into the trapping region. In ion traps a sequence of RF-voltages are applied to the rods (60) with increasing amplitudes and alternating phases. If the drag from the gas flow is stronger than the focusing force of the RF-field on large ions within the first trap, then only relatively small ions will be trapped in this RF-trap because the larger ions will be carried through it by the gas flow. The initial value and increments of the trapping RF-voltages for subsequent traps along the line of the gas flow (66) can be chosen in such a way that controllable different size separations would occur along the gas flow through all these traps. As the static gas pressure ($\sim 10^{-3}$ Torr) inside the gas flow (66) is significantly less than the pressure inside the trapping region (1) ($\sim 0.1$ Torr), neutral atoms coming with the gas flow into the trapping region will be concentrated inside the gas flow. Gas flows from mobility tubes (14) would push neutrals to the axis. After reaching the end of the trapping region and being reflected with gas flow from the warm wall 73) (set at about 100° C.) neutrals may come back against the gas flow due to diffusion, but the gas flows will turn them back to the axis of the trapping region. Thus the neutrals will be accumulated along the axis and smaller neutrals with larger diffusion coefficient will be located to the left while larger neutrals would be located to the right end of the trapping region. At any given time or frequency the accumulated neutrals may be ionized by a laser beam, electron beam, helium metastables, or by any other known means of ionization or ions and neutral may be fragmented by ionizing radiation from photons or particle bombardment.

FIG. 9 shows a cross-section of section AA in FIG. 8 which would incorporate four measuring units (400) in two opposing pairs. In order to prevent ions and neutrals from interacting during the accumulation, positive and negative ions are shifted from the axis (82 and 84) of accumulation region by DC-electric field (87) and are stabilized by RF-field (80) and gas flows (89). Neutrals are located around axis (83) as shown in FIG. 9. It is now possible to separately measure first the ions from the target (direct ions) and later ions from postionized neutrals. To do so, ions after their accumulation would be injected into two measuring units (400) located to the left (81) and to the right (88) of the trapping region. Ionization of neutrals by a post-ionization laser beam (86) follows only after the direct ions have all been trapped and injected. It is of course possible to use the same measuring units located at (81) and (88) to measure ions from neutrals and direct ions. First, direct ions are measured and only thereafter ions created from neutrals (e.g. post-ionized) are introduced into the measuring units. A new cycle of accumulation of ions and neutrals can start. Alternatively, two additional measuring units (400) located at the top (85) and the bottom (90) of the figure may be used to simultaneously measure both types of ions and thus shorten the analysis time. During the ionization of neutrals, a DC-voltage in the vertical direction (in the figure) is applied and a DC-voltage in the horizontal direction is switched off. So positive and negative ions from neutrals are accumulated and cooled at different locations and their mutual neutralization is reduced. After post-ionization, ions are directed to the corresponding planes of mobility tubes by increasing DC-field in vertical direction. Once ions are transported into the mobility tubes, both analyses of ions are taking place simultaneously (the analysis of direct ions may be started somewhat earlier) and another period of accumulation begins.

It seems at first that it is only necessary to measure positive ions created from neutrals since formation of negative ions during laser ionization is expected usually only by subsequent secondary electron attachment reactions. However, direct formation of ion pairs can occur, especially for the case of biomolecules which may exist in a preformed state within the sample in the form of zwitterions with equal number of positive and negative charges. Breaking bonds at different sites may produce such distinct positive and negative ion pairs giving valuable structure information. The energy of about 2 eV may be sufficient to break a peptide bond which thus can, depending on the particular structure of the zwitterion, create two separated ions of opposite sign. (Note, this can also be used to analyze the structure of ions where the net sum of negative and positive ions on the molecule differ by one or more charges). For direct ionization of organic molecule the energy of about 10 eV is necessary although this direct ionization by one or more photons often is accompanied by significant molecular fragmentation. A sequence where initially the accumulation of neutrals along the axis of helium flow through the trapping region based on their size related diffusion coefficient within the gas flow may be important for analysis of ions subsequently produced from these neutrals. Two ions of opposite sign which come from the zwitterions of some type should be correlated in the distributions for the ion beams (ideally should belong to the pair of corresponding ion beams) when simultaneously measured. This criterion, besides the assumption that each positive ion from a zwitterion should have the corresponding negative ion and sum of their masses should be equal to the mass of the zwitterion, may provide valuable information about the structure and sequence of these zwitterions. This could be important since often this information is difficult to obtain even when using CID or similar MS/MS techniques. Some difference in co-incident intensities of simultaneously produced ions from the zwitterion is possible due to different efficiency of ion trapping for negative and positive ions. Also secondary processes which further transform one or the other of the photofragment daughter ions are possible as well. Usually biomolecular zwitterions in the sample of natural origin have a distribution of charges and are not a single type of ions because they retain charges in different sites of the biomolecule according to a stochastic processes. So if a pair of positive and negative ions is suspected to belong to a zwitterion it is highly probable that positive and/or negative ions of the same mass (corrected for the number of attached or lost protons or, perhaps, alkali metals) would be recorded among ions coming directly from the MALDI target. Similar types of photo-fragmentation and coincidence between positive and negative structural fragments would also be expected from fragmentation of either the positive or negative ions when such ions had one or the other charge in excess in a structure which was charged at multiple locations. Thus if an ion which was for example nominally singly charged but contained a total of two positively charged sites and one negative, then the resulting fragmentation products could be either two "coincident" ions (one negative and one doubly charged positive), or one positive and one neutral fragment depending on whether the cleavage point was between the two positive charge locations or between the positive and negative charge location. Using four measuring units (81, 85, 88 and 90) provides better conditions for accumulation of neutrals around axis (83) because gas flows (89) from these units would force these neutrals to the axis from all directions. Furthermore, in addition to ions and neutral molecular species the MALDI plume can contain droplets or some large associations of molecules and ions. In such cases when the size of such particles is fairly large (1 µm or more), they cannot obtain significant velocity in the helium flow on such a short distance (about 2 cm). They may come to the right wall of the trapping region and can be accumulated there without evaporation of the solvent or significant degradation. Therefore it is reasonable to heat this wall to a temperature of about 100° C. or higher to evaporate the solvent from these droplets and release the neutrals or ions contained within. Ions and neutrals produced in such a way would be trapped in RF-traps or near the axis. It is probable in this case that ions would be trapped in the last trap (at the right of the trapping region) independently of their sizes. Detecting ions from this trap with and without wall heating would indicate the mechanism of droplet ion formation. It may also be reasonable to control the initial temperature of the gas (helium) to produce a fast narrow gas flow. In this case the divergence of the flow would not change much but the gas flow velocity would increase as thermal energy of the gas in this flow is transformed almost entirely into kinetic energy of axial motion of gas atoms. Droplets from MALDI target will be heated by the gas and may evaporate without freezing. This may produce additional ions and neutrals ready for ionization and thus enhance the sensitivity of measurements. The intensity and divergence of helium flow may be controlled by adjusting Pflow and Ppump—FIG. 8—(changing effective pumping rate) as well. Therefore, the neutral and ion trapping abilities and the distributions of trapped neutrals and ions along the axis can be varied. Switching off the helium flow removes all neutrals from the trapping region.

Figure 10:
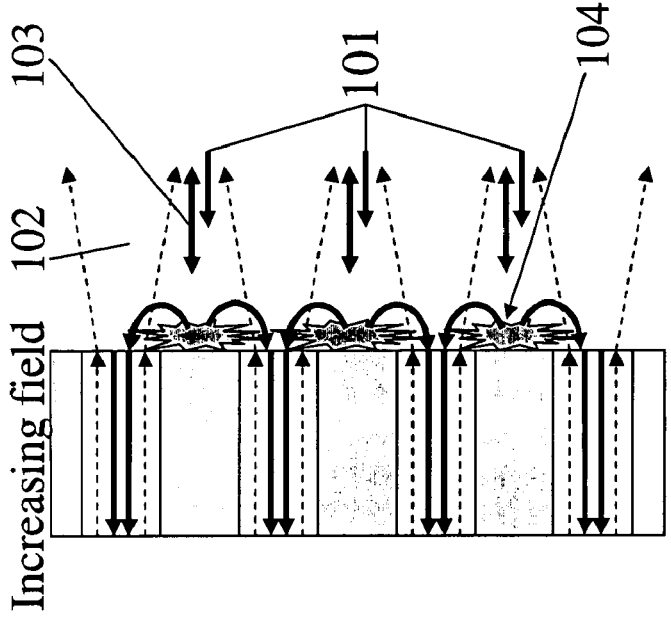
FIG. 10. Possible ways of trapping and inserting ions when MCPs are used for mobility separation.
Figure 10:
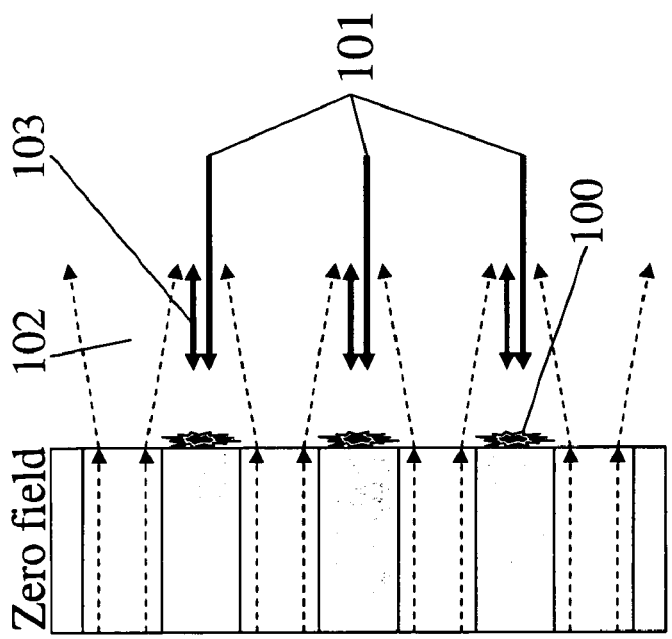

A possible way of re-trapping and gradually inserting ions into a multichannel structure (which might be for example microchannel plates used as mobility tubes) is shown in FIG. 10. Upon increasing the input DC-field (87) applied between collimated electrodes of both MCPs (97)—FIG. 9—ions come to the corresponding regions confined by collimating electrodes under opposite forces from RF-field (103) and the gas flows (102). (FIG. 10) Strong DC-field (101) created between collimating electrodes and corresponding MCP moves ions to the surface of MCP in spaces (100) between the channels. The absence of the field inside the channels and the strong gas flows diverging from the channels (102) make ions "stationary" in the front plane of MCP. A dipole field from the pre-charged dielectric coating of the MCP plane and strong DC-field from collimating electrode (4) prevents ions from moving away from near the MCP surface. Oscillations of ions under RF-field (103) are small and negligible. To insert ions inside the MCP, the accelerating DC-field inside the MCP is gradually increased while a DC-field (101) between the collimating electrode and the MCP is decreased. Ions under increasing influence of RF-field go from the surface (104) into MCP channels under the force from fringing field from these channels and begin to move inside them provided that the field inside the channel is sufficiently strong. Alternatively it is possible to accumulate ions before their insertion into the MCP (or other type of biasable microchannel array), directly in the regions confined by collimating electrodes. The external DC-field and RF-field are decreasing in these regions in a direction orthogonal to the MCP plane and the gas flow density is approximately the same at distances not too close to the MCP plane. It is thus possible to choose fields in such way that ions may become stationary inside this region and their positions would depend on the type of ions. To insert ions into MCP both DC-fields between collimating electrode and MCP and inside the MCP channels should increase simultaneously to initiate the ion motion into channels independently of their slightly different gas flow density. In this case the non-uniformity of fields may be the main limitation to the mobility resolution (the spatial width of the ion package at the exit of MCP). It is also obviously possible to use a single tube for each ion beam recording instead of a set of MCP channels. In order to keep all experimental conditions constant, the ratio of the tube diameter to its length should be the same as that of MCP channels and the orifice area should be equal to the total area of the MCP channels used for one ion beam. An electric field of controlled and uniform strength should be produced inside the tube. The plane in front of the tube and the conducting parts of internal surface of the tube should also be coated with a thin dielectric film not more than 1 μm and not less than 0.3 μm thick. It should be charged by the charges of the same sign as the ions with a density between $10^{10}$-$10^{12}$ cm$^2$. Inevitable difference between tubes for different ion beams could be numerically compensated based on calibration experiments when the same sample is recorded using all ion beams. As estimations show, the mobility resolution in this case is approximately proportional to the square root of the time of the separation, however, the separation time can not be taken too long due to loses of the trapped ions provided by the diffusion of ions against the gas flow in mobility tubes. So for the mobility separation time of several seconds the mobility resolution of a few hundred (for singly charged ions) may be possible.

Figure 11:
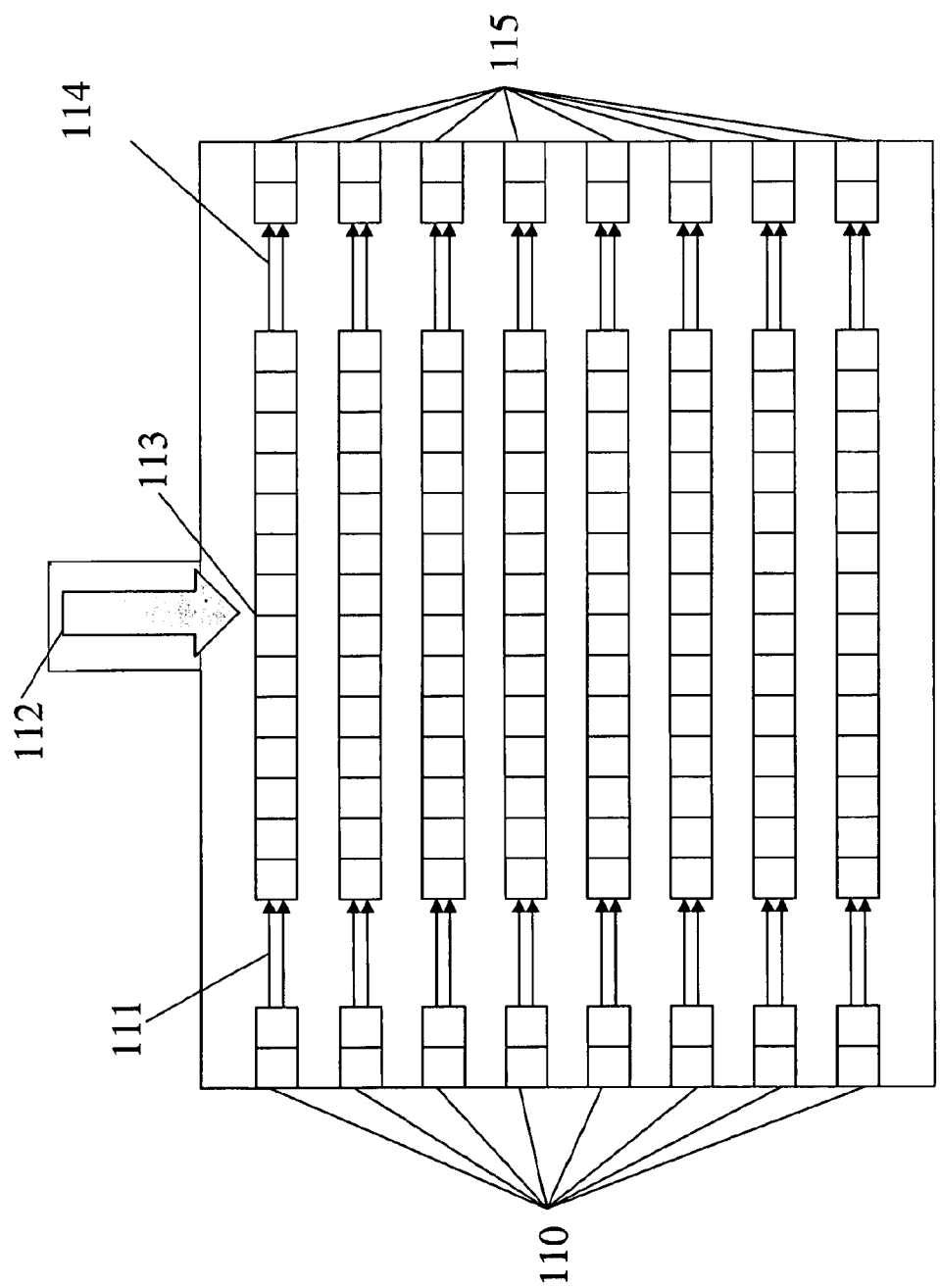
FIG. 11. Schematic view of the middle region of mobility cell where collision induced dissociation of selected ions is performed.

Helium flow (6) introduction and collision induced dissociation of specific ions can be performed in the set of CID tubes (FIG. 11). Exit orifices of mobility tubes (14) and entrance orifices of exit tubes (16) are open to this region to maintain the gas pressure near the orifices. Since all the channels for ion beams transport are supposed to work independently, any variation of electric fields in these channels should be done "locally", or at least without changing the voltages at the entrance of the corresponding TOFMS. In order to perform CID of ions it is impossible just to accelerate them by increasing electric field in a certain portion of the corresponding CID tube (15). A reverse field to decelerate ions has to be applied, which will also tend to defocus or even to stop them. The effective way to do that without ion losses is to apply such fields inside the tube whose internal surface is coated by charged thin dielectric film. As mobility separation of ions against gas flows may be done slowly (mobility peak widths of several milliseconds or more) there is enough time for CID of specific ions without losing mobility separation. When no CID is performed, the electric field inside CID tubes (15) can be linear and strong enough to essentially transmit all ions coming out of the mobility tubes (14). A strong accelerating field is applied to realize CID at the beginning of the tube. The same strength deceleration field is created at the end of the tube. The length of the strong field regions should be small enough to avoid the formation of a glow discharge (about 0.5 mm for 10 Torr helium). Upon switching on these fields, ions with possible CID products will be accumulated inside corresponding tubes and will come out in a short pulse after the fields re-set. The delay time for the recording of these ions may represent additional analytical information about these ions. It is reasonable to synchronize the time at which ions are released with the time at which TOFMS extracting pulses are applied to increase the dynamic range of data recording. Namely using different delays between the time of ion release from CID tubes and TOFMS extracting pulses it is possible to estimate the ion velocity of the fragments by comparison of shifts in peak location using position sensitive detection in axial direction. Using position sensitive detection for anodes shifted in orthogonal direction it is also possible for such conditions to estimate angular divergence of corresponding ion beams.

Multi-Channel Exit Interface

The separated ion beams as shown in FIG. 12 are directed after CID tubes into the exit sectioned tubes (16) with internal electric field of approximately the same strength as that inside the CID tubes. At the end of these tubes the helium flows (122) have a low divergence angle corresponding to the gas temperature of about 1K. Ions coming with this gas flow (120) are focused inside an RF multi-pole multi-channel ion guide. The rods of this guide (18) are supplied with RF-voltages of the same phase and amplitude. Ions are focused to positions around the points of zero RF-field (123). The plates (17) between the rod pairs provide focusing RF-field with the same phase as that of RF-voltage applied to rods. Since ions were mobility separated before coming to the interface, they have fairly low m/z values at the beginning of the measurement cycle and roughly linearly increasing m/z values during the cycle (with different slope coefficients for different types of ions). It is therefore reasonable to increase the amplitude (or decrease the frequency) of RF-voltage applied to rods proportionally to the square root of the time since the beginning of the measurement cycle with the coefficient being the square root of the slope of the m/z versus drift time to more nearly match the RF characteristics to exactly transport the mobility selected ion size which happens to be in the RF cooling region at that time. This RF-field variation would allow to record small ions without defocusing and losing them due to possible instability of their motion in a large amplitude (or low frequency) fixed RF-fields.

The RF field variation would also give an opportunity to effectively focus large mass ions to the same beam width as smaller ones. This is true for the singly charged ions; moreover multi-charged ions will be focused even better—proportionally to the charge. When the CID tubes are used to form CID products, it is important to point out the following. CID is usually used to obtain structural information about ions and the most valuable information is obtained from fragments with masses close to that of the parent ion. Ions moving with gas having 1K temperature and focusing in RF-ion guide come closer and closer to thermal equilibrium with the gas and their temperature becomes low. Since the width of an ion beam focused in a RF-ion guide is proportional to the square root of the ion temperature, the ion beam width may significantly decrease. For example, ions having 3K temperature would have the final beam width 10 times smaller than that of ions at room temperature (~300K). It is possible to obtain ion beams much less than 1 mm in diameter for room temperature RF-quadrupoles, the beam width of low temperature ions may be less than 0.1 mm. If input orifices in TOFMS (130) can be about 0.1 mm in diameter, low gas flow (122) will penetrate inside TOFMS and the desirable low gas pressure inside TOFMS may be provided by using relatively modest pumping power.

oTOFMS Suitable for Multi-Beam Ion Recording after Ion Cooling in the Exit Interface If ions coming from the exit interface (FIG. 12) have low divergence and the velocity close to that of the helium flow (about 1400 m/sec at room temperature) it is not necessary to accelerate and focus them additionally. Moreover, these attempts may spoil the desirable properties of the parallel cooled ion beam due to inevitable non-uniformity of electric fields. As shown in FIGS. 1 and 12 the regions from the end of the exit tube (16) throughout the regions for RF cooling (8), the region (127) containing differential pumping and ion mirrors (20,21) and finally into the oTOFMS. The same DC-voltage U1 is applied throughout. From the end of exit tube (16), to the multi-pole ion guide (17,18), to the mirrors (20, 21) and the oTOFMS (124) itself there exists close to a zero-field region so as not to affect the trajectories of the nearly perfectly cooled ion beam (132). Thus once the cooled ion beam is formed and reflected it is kept as undisturbed as possible. It will be nearly parallel in the vertical plane (FIG. 12) but divergent in the horizontal plane (FIG. 11). (The divergence in the horizontal plane could also be corrected by using a perfect parabolic shape for mirror element (20) instead of the cylindrically parabolic which is illustrated).

The fact that the velocity distribution of ions is made equal to the velocity of the He by the RF cooling in region 8 gives virtually the same velocity to all ions over a wide mass range. This narrow, mass independent velocity distribution allows better use of the ion accumulation time in the extracting region. The problem usually encountered in orthogonal TOFMS is that ions with medium to larger masses are detected with better efficiency than lower mass ions simply because the low mass ions (when compared to the slower velocity large ions) move quickly through the orthogonal extraction region and are mostly lost. Also, losses of really high masses falls off in part because these ions are moving so slowly that it takes a very long time to fill the orthogonal plates and, therefore, a large fraction of these larger masses do not have time to adequately fill the region between the orthogonal extraction plates and are lost at the front region of the extractor. On the other hand, a potential problem with the present invention is that because the flight time through the analyzer is correlated to the ion velocity in the initial direction of ion motion (in case of ion acceleration by electric field) the reflected ions with axial velocity close to the drift velocity of the gas may partially or entirely miss a detector which is located coaxially with the extractor plates. To overcome this drawback it is possible to tilt the ion mirror with respect to the ion flow/extraction plates and place the detector parallel to the extraction as it is suggested, for example, in the U.S. Pat. No. 6,683,299, K. Fuhrer et. al., 2004, incorporated by reference as though fully described herein.

Another way to avoid missing the detector is to use a Linear TOFMS (right-bottom part of FIG. 12 and FIG. 13A.B) with orthogonal injection of ions—LoTOFMS. In this case there is no problem with recording ions of all masses. The cooling and focusing into very cold parallel beams as described in our invention will result in acceptable mass resolving power in a very compact linear TOFMS instrument. The theoretical estimations show that if ions (132) are accelerated by a uniform electric field in the region (131) which is two times shorter than the field-free region (130), they would have the same time of flight to the surface plane of a micro-channel plate, MCP, detector (135) located at the end of this drift region (130). In the first order of approximation for zero initial velocity transverse to the beam direction (zero turnaround time) ions of specific m/z would be perfectly time focused at the MCP detector (135) surface. regardless of their starting positions. Below the detector MCP are shown multiple anodes (129) for position sensitive detection and for detecting simultaneous multiple ion arrivals at any particular m/z. If ion kinetic energy of random motion in the direction of acceleration corresponds to the temperature, which is about 1K, the mass resolution would be between 4000 and 5000 for 5 kV acceleration voltage (path length of ions may be about 20 cm or less). Using parabolic (or quasi-parabolic) mirror (20) made of conductor coated by thin charged dielectric film the divergence of ion beam (132) may be significantly reduced further so it may be possible to record high resolution time-of-flight mass spectra (more than 10000) with this compact linear instrument (about 20 cm long).

Figure 13:
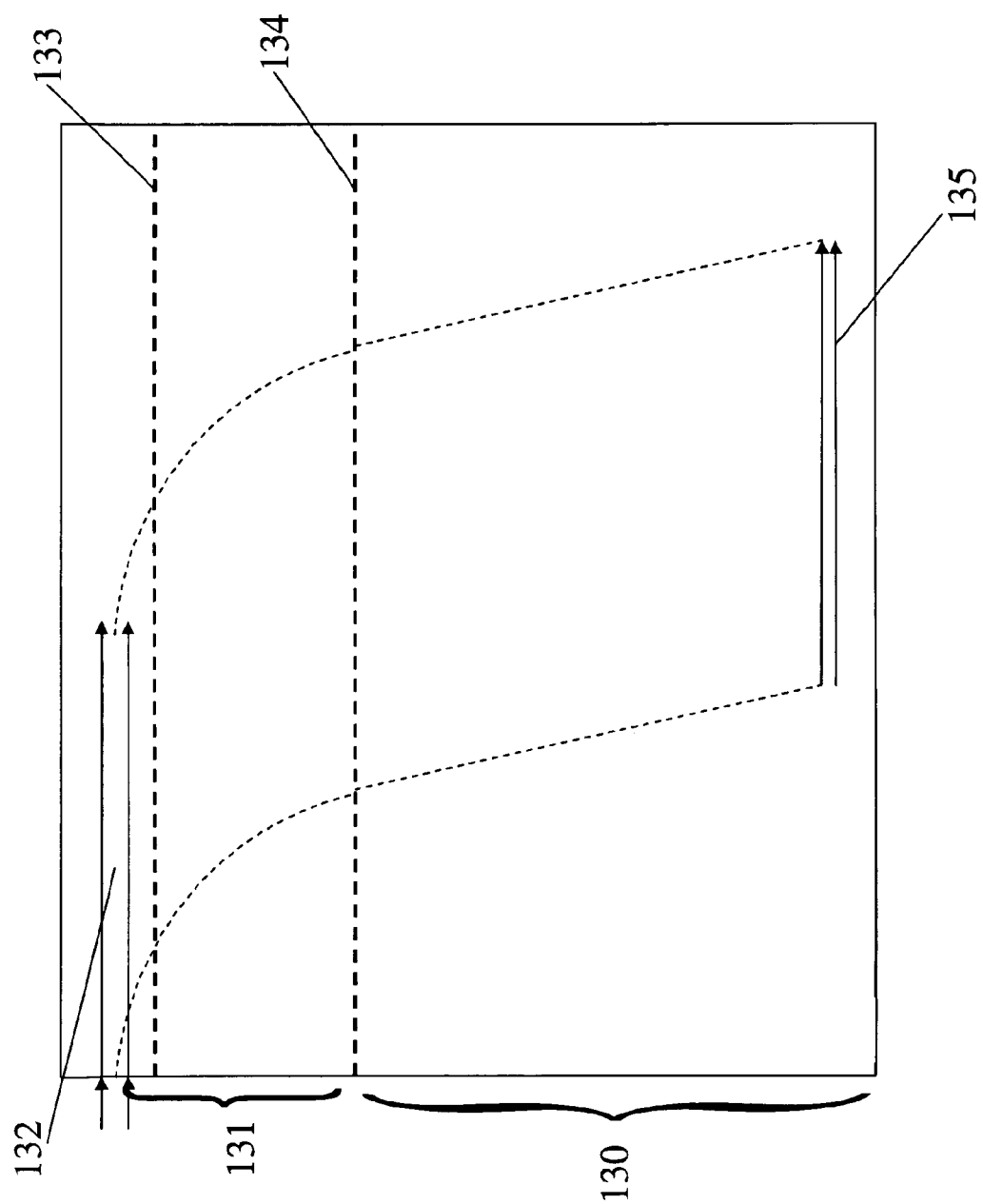
FIG. 13. Schematic view of the linear TOFMS collecting and mass analyzing multi-ion beams.

To decrease the "dead" time for inserting ions into the acceleration region (131) of FIG. 13 a grid (133) may be used in the following way. At the beginning of ion acceleration voltages are applied to electrodes (126, 133, and 134) to create a uniform field between plates (126) and (134). The potential of grid (133) therefore should be equal to the potential of the uniform acceleration field at this position. After the ions with largest possible m/z go through grid (134) the potential of (133) and (126) is changed to that of the input orifice (121) (U1). A new portion of the ions (132) may then penetrate inside the acceleration region of the instrument. Zero field strength in the region (130) is always necessary.

A grid free operation of the instrument (FIG. 13B) is also possible due to relatively small width of the ion beam (132) in the plane orthogonal to ion acceleration direction (at least for a single beam LoTOFMS). The necessary electric field may be provided by corresponding potential differences between frames (136) confining acceleration region instead of by grids. Voltages applied to the frames may be found by the computer program to provide minimal average squared deviation of the actual field potential distribution along the trajectory of ion acceleration from the ideal expected distribution. In this case after filling the chosen interval with ions (132) the field inside the region (131) for ion acceleration should be switched on for the time necessary to pass the border (112) of field (131) and field free (130) region for heaviest ion expected in this package of ions and the next cycle of ion (132) accumulation could be started after the field switching out. It is possible to form instead of "uniform" field in the region (131) and "zero" field in the region (130) a parabolic field in the whole volume of LoTOFMS from the plate (126) to the recording plate (135). For ideal parabolic field spatial ion focusing would be ideal instead of first order focusing for the previous piecewise-linear field. The necessary voltage distribution for the frames to approximate such field can be found by the program mentioned above used for constructing of a piecewise-linear field. Such field should be switched on for the time necessary for the heaviest ion expected in the current package of ions to be recorded and be switched out for the time of accumulation of ions (132).

Reduced pumping requirements for achieving high vacuum inside the LoTOFMS (124) is a further advantage of this arrangement shown in FIG. 12. After reflecting the cooled ion beam (123) from the parabolic (20) and flat mirrors (21) the parallel ion beam (132) is shifted vertically from its initial direction of motion but the gas flow (128) is randomly reflected from the parabolic mirror and may be effectively pumped. Small additional pumping would provide high vacuum inside the TOFMS.

Measurement of Beam Divergence Using Multianode Data Recording

Ion beams coming into the TOFMS have the width of about 1 mm and the average divergence of about 0.01 radian. As simulations show, the axial energy for large ions from such a gas flow is gradually increasing with their size and the beam divergence is decreasing. If the orthogonal extraction duty cycle of TOFMS is about 30 μsec then for a linear TOFMS ions fill the extraction region for 15-25 μsec and then travel in the TOFMS for less than 30 μsec. If ions have an axial velocity of about 1000 m/sec they will shift in this direction by about 5 cm and the standard deviation of the ion beam width in the plane of recording (due to 0.01 divergence) will be about 0.5 mm. If the distance between ion beams is about 2 mm these beams will overlap to some extent at the end of recording plate. Thus if the detector has eight anodes and each one is used to record an individual ion beam, it will record certain amount of signal from the adjacent beams too. This apparent drawback may be turned into an important advantage. A relatively small part of each ion beam is recorded on adjacent anodes. We can use this to increase the dynamic range of measurements when the signal in the main channel is saturated. It is formally the same concept as that of using two anodes of large and small sizes to intercept different fractions of the ion flux on the detector (see our U.S. Pat. No. 6,747, 271, Gonin, et al, 2004). With good m/z and mobility separation and several adjacent anodes for ion recording the problem can be solved in many cases.

Figure 14:
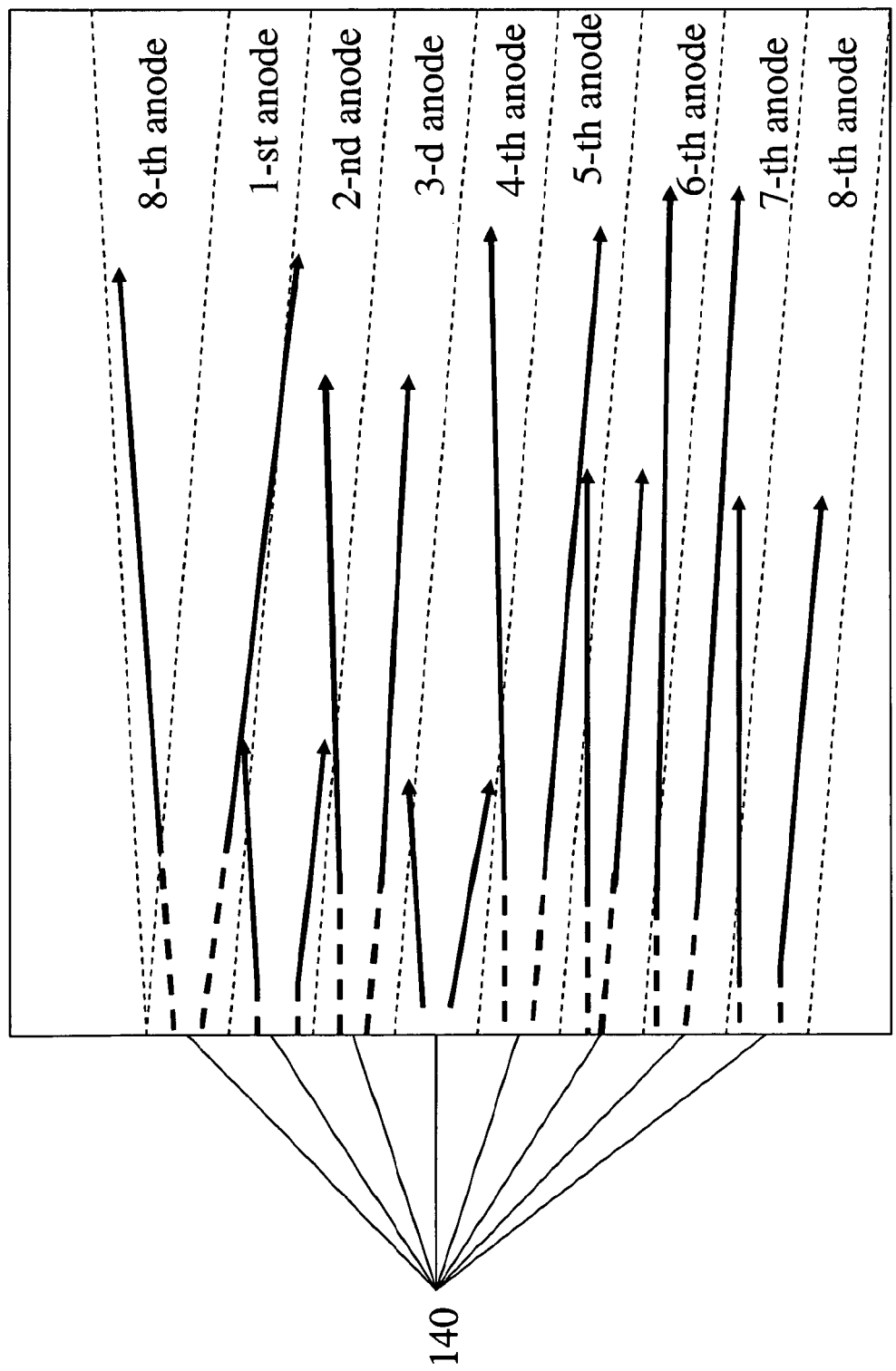
FIG. 14. Schematic view of the plate used to record separate ion beams in the TOFMS.
Figure 15:
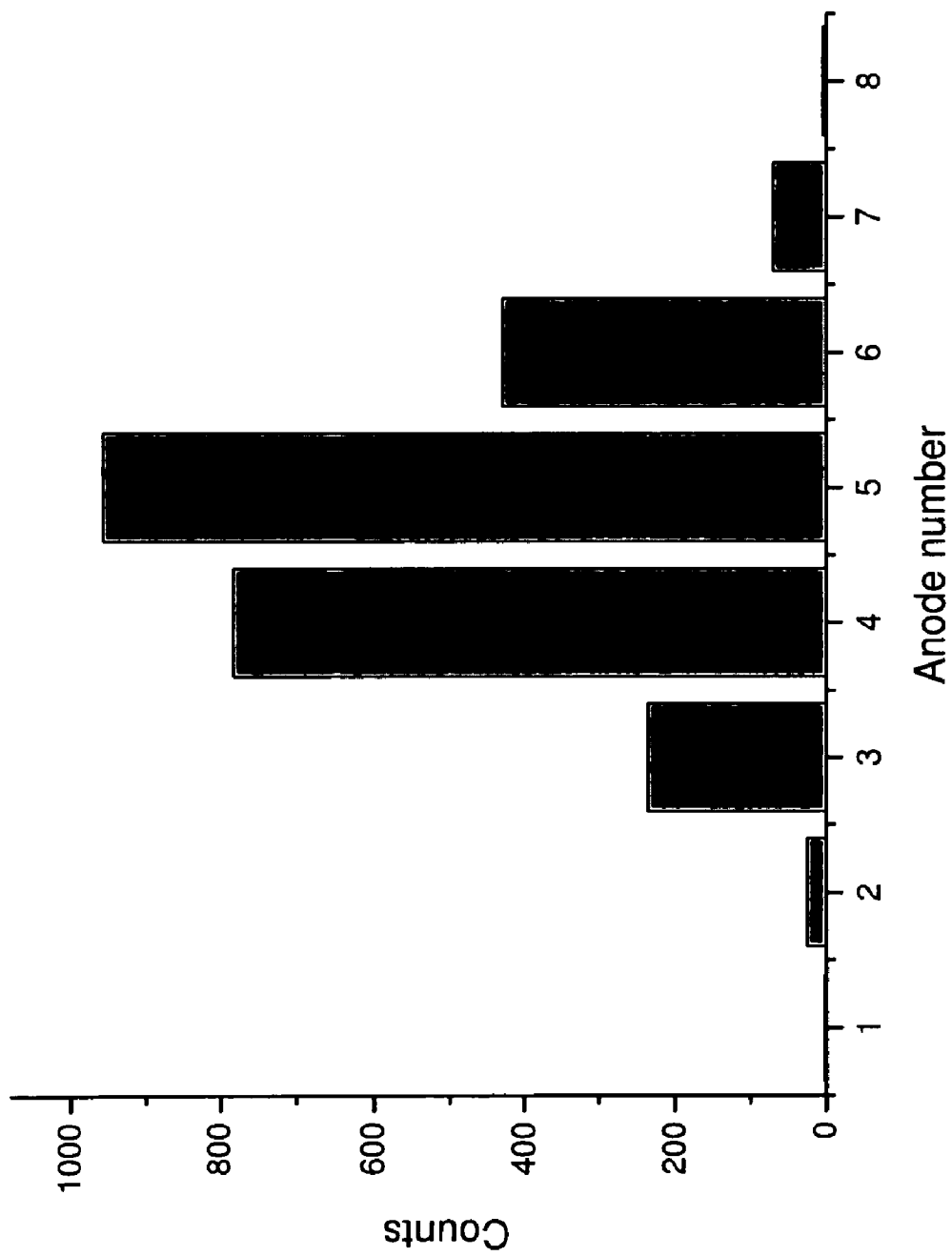
FIG. 15. Possible anode distribution of ion counts for the fifth ion beam.

Sometimes overlapping ion peaks may prevent precise measurement of the individual intensities but this situation is quite common in mass spectrometry and may be solved either completely or at least to some extent by deconvolution and curve fitting taking into account individual peak shapes and isotopic distributions. The same mass ions coming from different channels under the same starting conditions may appear at different times on the same anodes (due to mechanical inaccuracy, for example) and the corresponding peaks may not overlap. The coefficients for recovering the saturated signal in the main channel may be obtained by comparing the signals on anodes collecting the tails of mobility peaks (i.e. where the main signal is not saturated yet). These coefficients for known location and sizes of recording anodes could be converted easily into the angle divergence of ion beams if the velocities of ions in axial direction are known. It is possible to obtain velocities by using signals from several (two or three) separate anodes. These anodes should divide the expected spread into equal parts. The signal from each part with the signals from adjacent channels would allow estimation of the average axial velocity of a given ion of as well as its angular divergence or temperature. These two values (the axial velocity and the temperature of ions for specific experimental conditions) may provide additional information about ions which does not strictly depend on their m/z ratio and mobility. Ion velocity would be mainly determined by the ion mass and its cross-section for collisions but this cross-section may be different from the mobility cross-section. Since ions move in a very cold gas, they will be significantly cooled and their conformation may change. They may become more compact and have a noticeably smaller cross-section compared to that at higher temperatures. It is possible to get some additional information about the shape of these cooled ions by measuring their ion velocity and angular divergence using only eight anodes and recording eight ion beams. The corresponding anodes should be located at a certain angle relative to the direction of ion beams as shown in FIG. 14. In this case, the distribution of ion counts for each ion beam (140) over all anodes (as shown in FIG. 15 for the fifth ion beam) would be shifted from its maximum position on the corresponding anode. The higher the average velocity is, the larger this shift would be. The distribution width will characterize the divergence of the ion beam. Since ion propagation can be described by a simple function, it is possible to get quantitative estimations for both ion average velocity and the angular divergence of the ion beams by fitting theoretically predicted data with experimental ones.

In case angular divergences of ion beams on the detector are too low to provide convenient increase of the dynamic range of the measurements it is possible to either provide more anodes and/or to produce a non-uniform focusing of the ion beams. Ion divergence in the direction of ion orthogonal extraction should be as small as possible to get high resolution whereas divergence in the orthogonal direction may be significantly large. To obtain such focusing, the multi-channel RF-ion guide rods (18), as in shown at the top of FIG. 12, may be constructed to be closer in the vertical direction but at a larger distance in horizontal direction. In this case, the profile of ion beams (123) will become stretched in the horizontal and flattened in the vertical direction. Thus less ion cooling will be provided in the horizontal direction while maximum cooling will be produced in the vertical direction. Final parameters for the RF-ion guide should be found using computer simulations. Another possible result of ion cooling, at least for biomolecular ions, is that in folding processes some helium atoms may be caught inside the folded structure. Therefore, formation of clusters with helium atoms is possible for certain conformations. To some extent, the degree of ion cooling in the gas flow may be varied by changing the field strength inside the exit tubes. Ion beam divergence, their velocity at the end of RF-ion guide and the cluster distribution may be changed to some extent by application of corresponding electric fields.

Recording of Elemental and Molecular Ions Using SIMS

Figure 16:
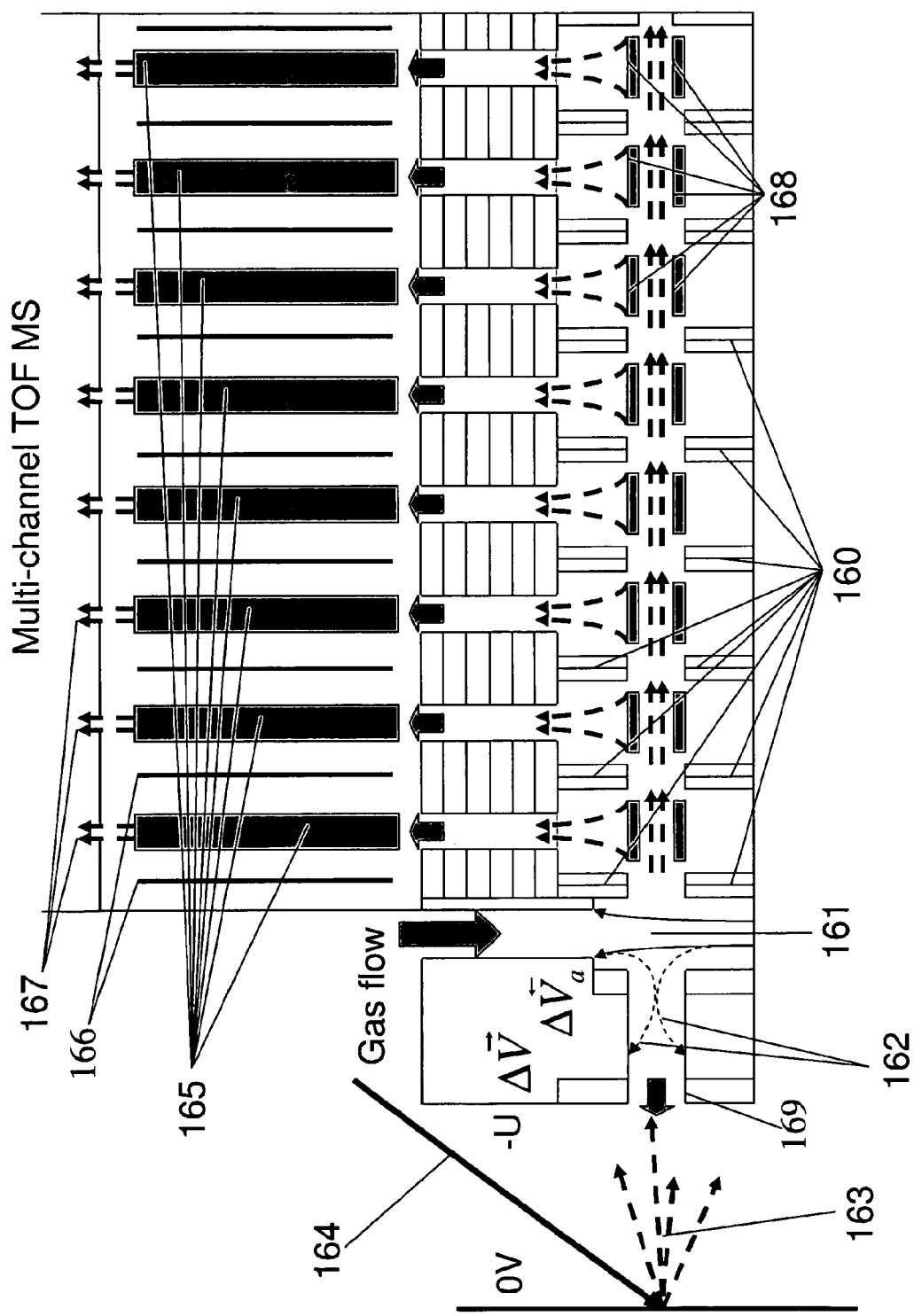
FIG. 16. Multi-beam TOFMS entrance interface for SIMS measurements with separation of ions according to their kinetic energy.
Figure 17:
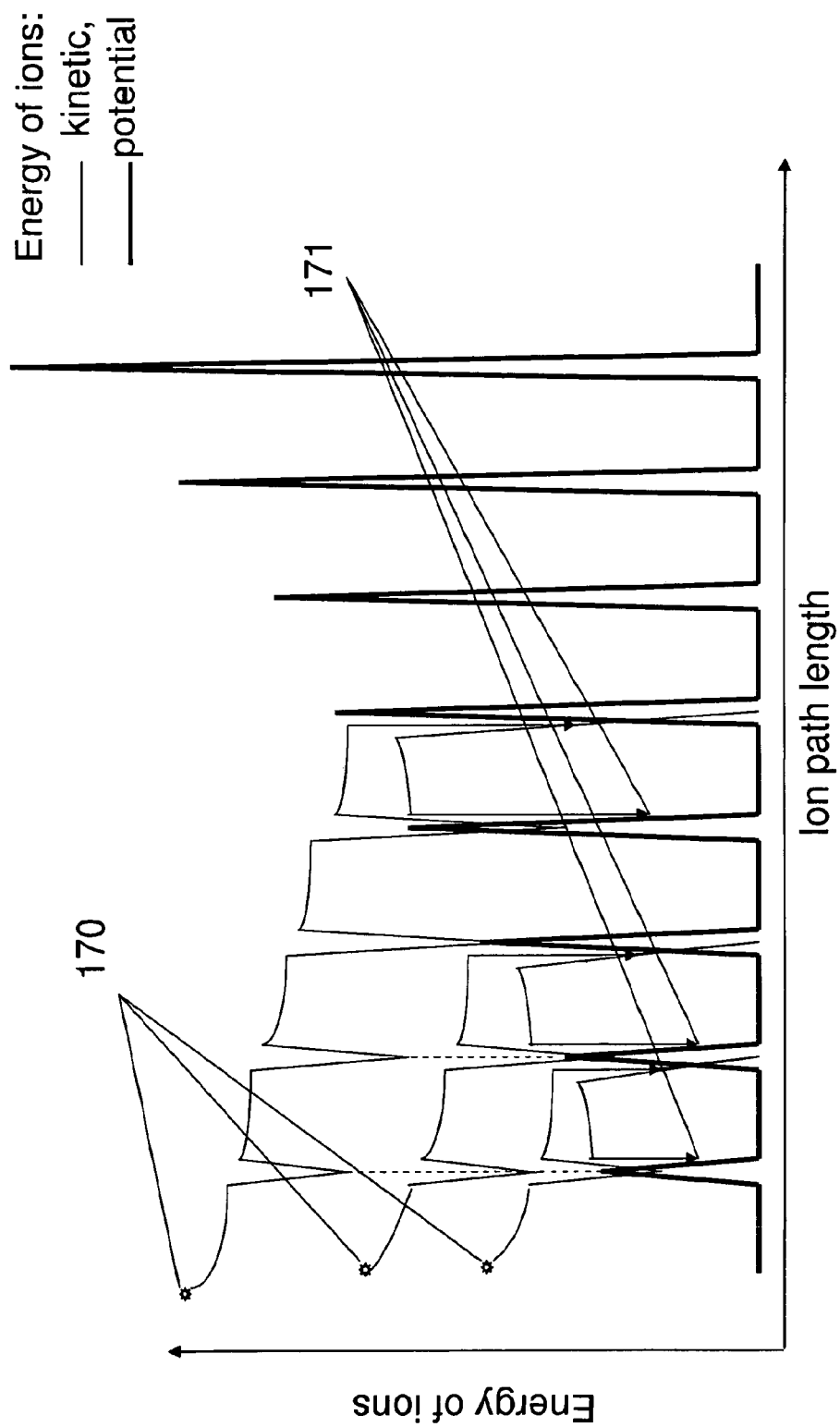
FIG. 17. Retarding and locking potential distribution and changing of kinetic energy of ions coming into the trapping region of the interface shown in FIG. 16.

FIG. 16 schematically shows a multi-channel TOFMS entrance interface for secondary ion mass spectrometry (SIMS) measurements of elemental or molecular ions liberated from a surface by impinging energetic primary ions (these including a wide variety of cluster and solvent droplet ions known to those skilled in the art). The liberated secondary ions have relatively large energy spreads of several tens of electron volts. Positive ions (163) coming from the surface after the primary ion (164) impact, are accelerated by the potential −U towards to the input tube (169) of about 1 mm diameter against a gas flow coming from this tube, ions are focused into the tube by additional potential difference −ΔV applied to adjacent two section electrodes at the exit of the tube. A portion of neutrals formed under SIMS conditions can also enter the tube. To ionize the desorbed neutral elements, helium ions (162) produced in glow discharge (161) just before the entrance of the tube are accumulated inside the tube up to a steady concentration. The potential difference at the exit of the tube $-\Delta V$ prevents them from going out of the tube. The potential difference at the entrance of the tube $+\Delta V$ (which should be somewhat less than $\Delta V$) controls the concentration of accumulated helium ions. The internal surface of the electrically conducting tube should be coated with a dielectric film to prevent loss of helium ions on the surface. Conducting material of the tube would generate image negative charges to ions inside the tube, which significantly compensates for the influence of the space charge. Thus a large amount of helium ions could be accumulated inside the tube to provide ionization of practically each neutral particle entering the tube. Ions exit the input tube and enter an ion trapping region as they have sufficient energy to overcome the retarding potential of the first triad electrode of this region. Due to the retarding and locking potential differences applied to electrode triads (160), ions with energies in a certain chosen intervals are trapped inside RF-quadrupoles (168) located between these triads with the exception of the last one which has only a pair of retarding electrodes (on the right side) (169). Alternatively, well established techniques for laser post-ionization of sputtered neutral elements may be employed. FIG. 17 schematically shows how the ion kinetic energy in axial direction (170) changes when ions are moving along the trapping region. There is only an exponential damping of ion kinetic energy in the intervals where the axial electric field is absent. The energy is sharply decreasing when ions are moving between electrodes where retarding potential difference is applied (the first and the middle electrodes of triad electrodes (160)). The energy is increasing when ions, after overcoming a retarding potential difference, are moving in the field created by locking potential difference between the middle and the last electrodes of triad electrodes (160). Due to some ion energy losses from collisions with gas atoms, ions could have somewhat reduced energy compared to the energy that they had before the retarding gap. Ions further lose their energy in gas collisions and come to the next retarding gap. They are reflected back and trapped (171) inside the corresponding RF-quadrupoles (168) in case where their kinetic energy is insufficient to overcome the locking potential difference at the beginning of this RF-quadrupole. The retarding potential difference at the end of each RF-quadrupole and locking potential difference at its beginning should be close enough to trap ions. The difference between them preferably should not be significantly higher than the ion energy loss from collisions with gas atoms on their way back in RF-quadrupole after reflection from the retarding potential. Otherwise ions could come back from RF-quadrupole to the beginning of the trapping region and information about their energy will be lost (although the energy distribution of the secondary ions is seldom used analytically). It is probable that some ions from the target and some ions produced from neutrals will not be able to enter the trapping region due to lack of initial energy. They will be trapped inside the input tube and can be analyzed separately if primary ion bombardment and glow discharge are stopped, and if potential differences along the input tube pull them out of this tube. Helium ions also coming from the tube will not be trapped inside RF-quadrupoles (168) due to their low m/z value and will be preferentially discharged on the rods of the first RF-quadrupole. Trapping of the "remaining" ions in several RF-quadrupoles will be useful to obtain large dynamic range data. Some estimation of collision cross-section of the recorded particles will be also measured in this case, which would allow to reconstruct initial energy distribution of ions previously recorded. By switching out of RF-voltages in quadrupoles (168) and switching on the corresponding DC voltages between their rods, adjacent electrodes of triads (160) and permanent strong axial field inside sectioned tubes (16) accumulated ions are inserted (158) into these tubes. As before the tubes (16) produce supersonic gas flows (122) which move ions through multi-beam RF ion guide formed by RF-rods (18) and confining plates (17) with zero or constant voltage. After this ion guide well collimated and low divergent ion beams (123) are inserted into multi-channel TOFMS.

Recording of Ions and Neutrals from Spray Ion Sources (Electron, Pneumo, Laser)

Figure 18:
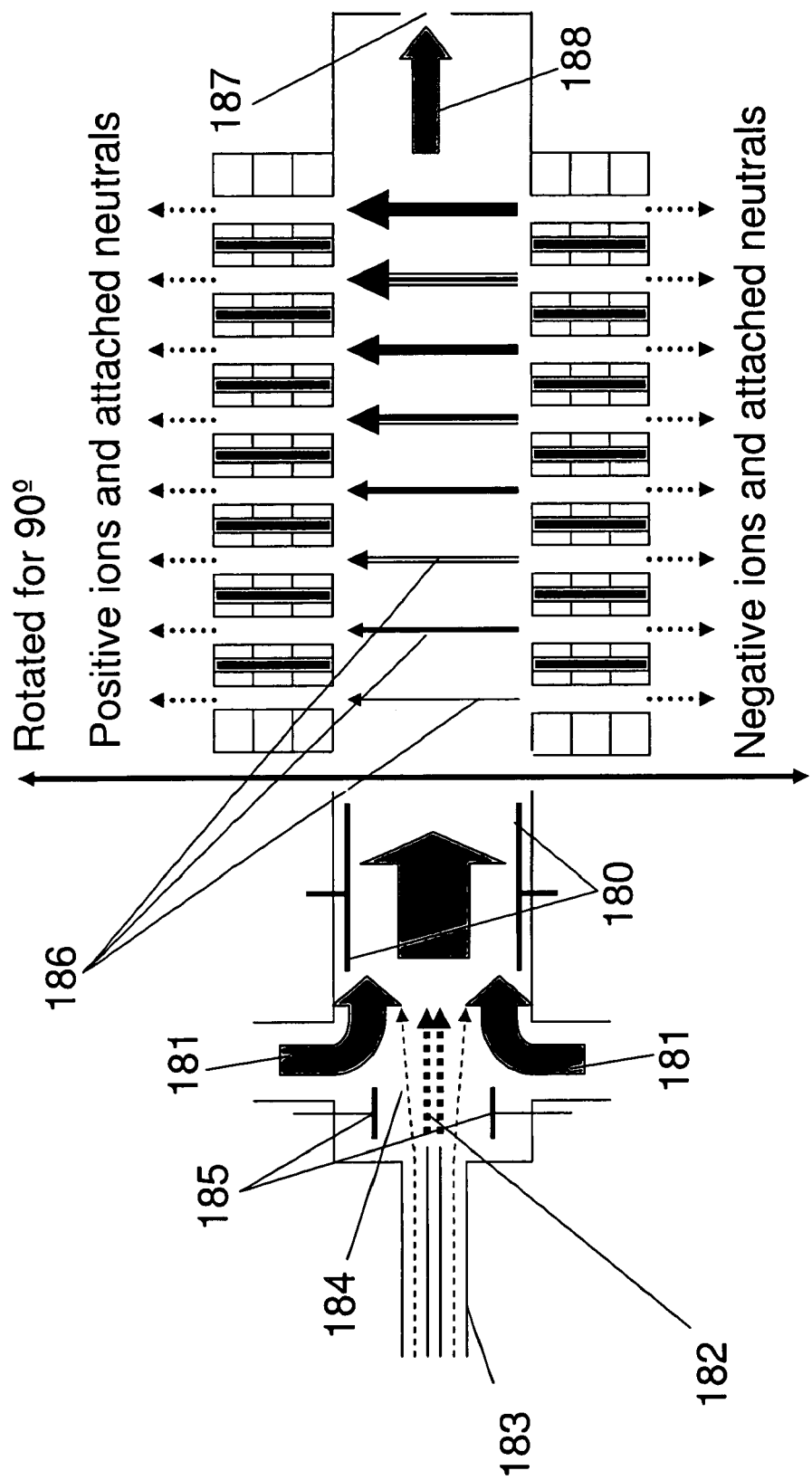
FIG. 18. Schematic view of the proposed electrospray interface.
Figure 20:
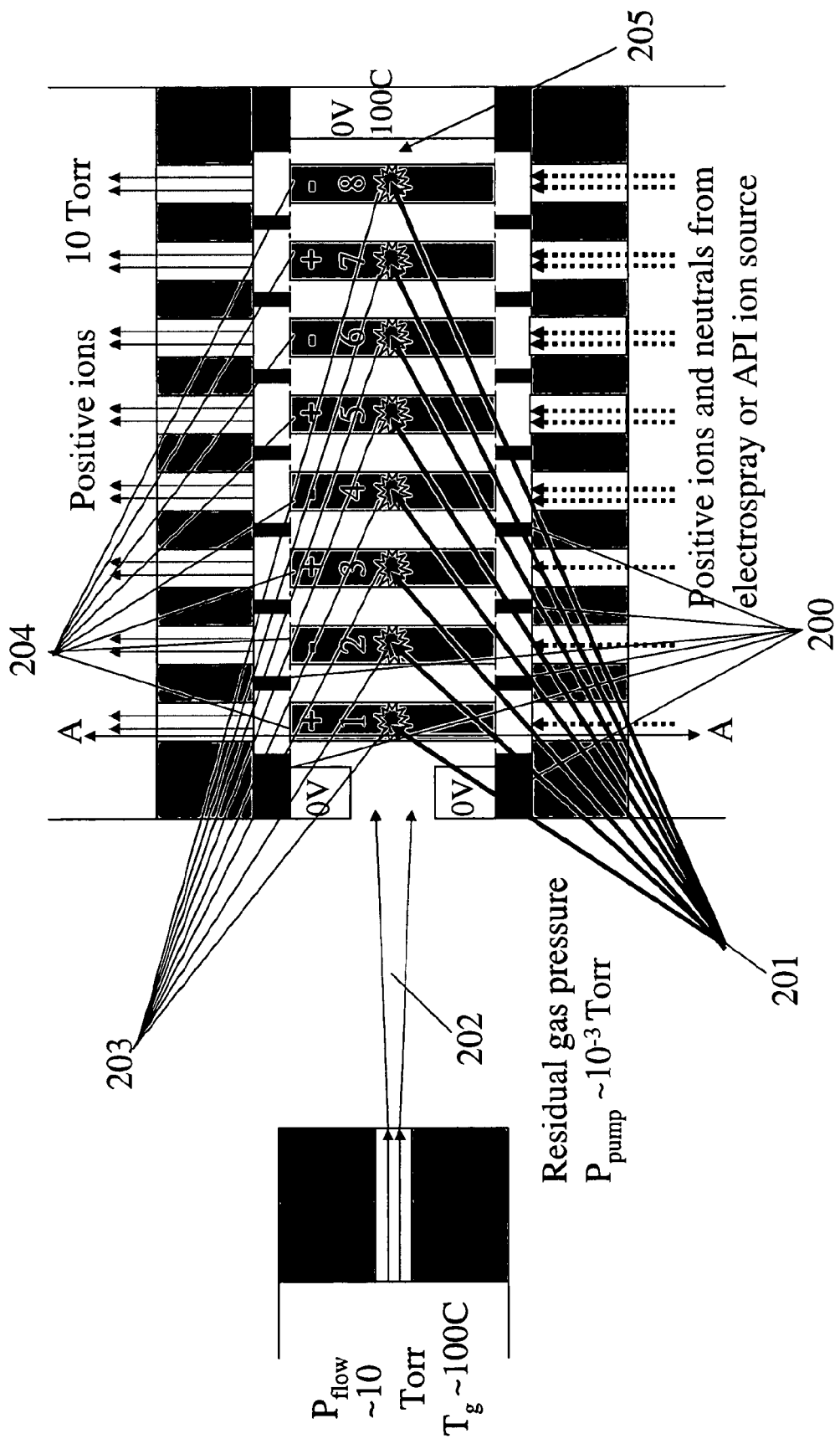
FIG. 20. Schematic diagram showing a multi-beam storage device for positive ions and attached neutrals from electrospray or corona discharge ion source with post-ionization of neutrals. The same storage may be used for negative ions and attached neutrals by inverting the electric field polarity.
Figure 21:
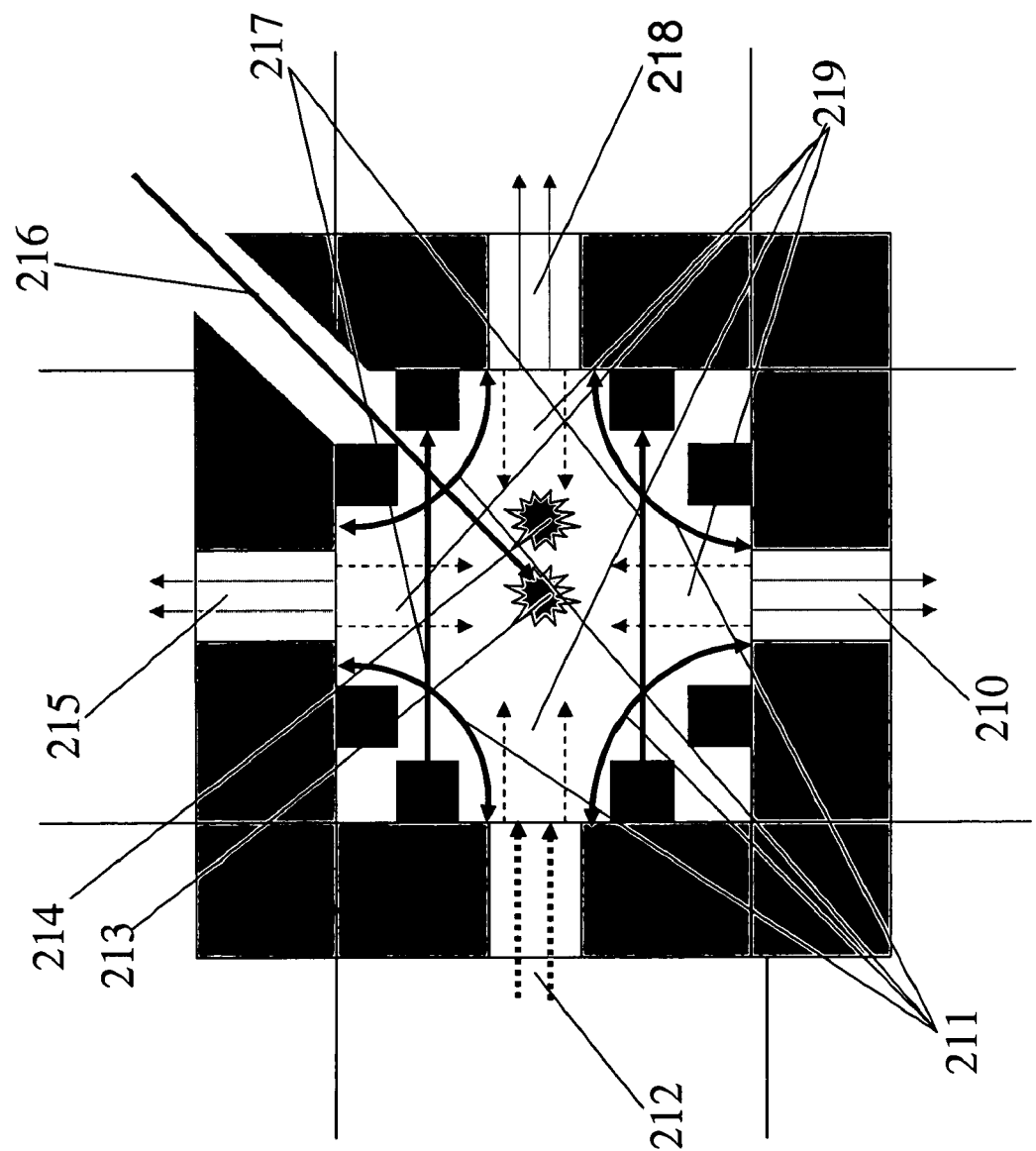
FIG. 21. Section A-A from FIG. 20. Neutrals are trapped in the center, positive ions are shifted to the right.

FIG. 18 shows schematically the first part of the proposed entrance interface for multi-channel mobility TOFMS using electrospray, pneumo-spray, or laserspray ion sources. Typically, the formation of the flow of droplets (182) from the input capillary (183) is provided mainly by the nebulizer gas flow (184). To overcome the main drawback of such type of droplet formation, i.e. the fact that droplets carry no charge, one may apply sound frequency voltage (185) as shown in the figure. If the frequency of this voltage is chosen to be close to the eigenfrequency of droplets' oscillations it will be possible to split specific sized droplets into pairs. One droplet in each such pair will have some excess of positive charge whereas the other one will be negatively charged. Thus the conventional mechanism of droplet evaporation and further splitting proposed for a typical electrospray ion source can be initiated on demand. Further evaporation of the solvent from these droplets is stimulated by heating of these droplets by microwave influence (180) and hot gas flow (181). Hot gas is inserted from two opposite directions orthogonal to the flow of droplets. A microwave electric field may be applied in these directions as well. Microwave heating of droplets has significant advantages in comparison to conventional use of hot gas flow. As the transfer of energy from hot gas to droplets is proportional to the droplet surface, it is less effective for evaporation of large droplets. In contrast, microwave energy flow to the droplet for small droplets is proportional to the volume of the droplet. So it has nearly the same efficiency for evaporation of each droplet. This energy flow is easily controlled, takes less power and does not significantly heat other parts of the system, for which heating is not desirable. In the plane orthogonal to the direction of hot gas insertion, ions and charged droplets of opposite signs are moved by increasing electric field (186) into capillaries which accept a certain number of gas flows (eight are shown in the figure) with positive and negative charged particles. Increasing electric field between opposite capillaries results in collecting different fractions of the charged particles into these capillaries. Low volume-to-charge ratio particles will come inside the left (as shown in the figure) capillaries and the particles with larger volume-to-charge ratio will be directed into capillaries on the right. Large droplets with small charge and neutral droplets which were not caught by any of capillaries will come with the remaining flow (188) through a changeable external slit (187). This changeable slit would allow controlling the portion of the gas flow directed into capillaries. The capillaries can be made out of sections of insulator plates coated by thin metal film so that voltages applied between these sections would provide good focusing of charged particles inside these capillaries close to their axes and their heating by collisions with gas. Neutral species attached to the ions may be removed in controlled fashion from these complexes and will come into the trapping region with gas flow as shown in FIG. 20 (for positive ions). The same trapping region is supposed to be used for negative ions with inverted DC-fields. This part of entrance interface for multi-channel mobility TOFMS is very similar to that proposed for the MALDI ion source. The main difference is that one TOFMS is absent in this case. Instead of supplying TOFMS with corresponding ions the flow of ions and neutrals from the electrospray ion source is coming inside this trapping region. The cross section of this trapping region for this case is shown in FIG. 21. Analysis of neutrals attached to ions separately for positive and negative ions may be useful as these neutrals may be different for different type of ions and investigation of so called non-covalent complexes of biomolecules and ions relevant to some applications may be realized.

Recording of Ions and Neutrals from Atmospheric Pressure Ionization Ion Source

Figure 19:
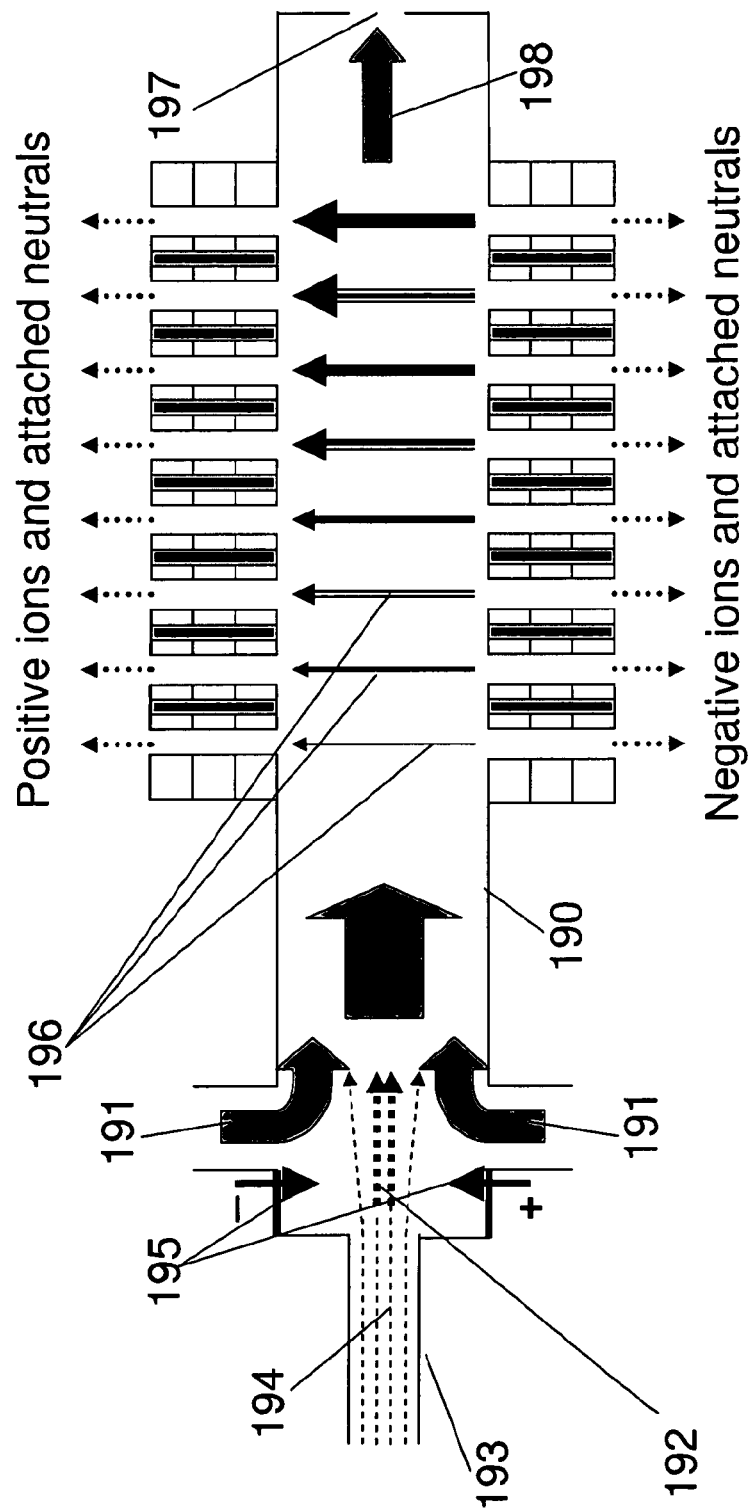
FIG. 19. Schematic view of the proposed corona discharge API interface.

Almost the same entrance interface may be proposed for an atmospheric pressure ionization source for direct analysis of admixtures in ambient air. FIG. 19 shows the first part of this interface. A bipolar corona discharge (195) can be used (other sources may be used too, for example, a radioactive foil) to produce ions (192) from neutral admixtures coming through capillary (193) with air flow (194). Flow of hot dry gas (181), for example, nitrogen, will prevent formation of large cluster ions. Admixtures having less proton affinity than H2O molecule or electron affinity less than OH radical can not be formed as separate ions in significant amounts but they may be attached to other ions. Therefore, investigation of neutral species attached to ions may be important for some applications. As in the case of electrospray ion source, ions combined with the gas flow through the tube (190) are coming into the separation region where under the influence of increasing electric fields (186) they are inserted into the corresponding capillaries. The gas flow containing neutral and low charged large particles (188) is coming through the exit slit (187). The same second part of the entrance interface, which is used for the electrospray ion source shown in FIG. 20 and in FIG. 21, may be used for atmospheric pressure ionization source as well. Since the formation of ion pairs is possible for some neutral species in air, the analysis of ions of both signs produced from these neutrals may be important. For specific applications this interface can be simpler, when analysis of neutrals or when analysis of ions of a certain sign are not required.

The details in the FIG. 20 and FIG. 21 (partly coinciding with FIGS. 1, 7, 8, 9 and 10) are as follows: (4) are the collimating electrodes for collecting ions into corresponding traps and mobility tubes. (86) are laser beams for post-ionization of neutrals. (66) is the well-collimated gas flow for trapping neutrals along the axis of trapping region. (2) are the ions trapped by increasing RF-voltage with alternating phases applied to stripes (60). (1) is the trapping region where gas pressure of about 0.1 Torr is maintained. (90) is negative ion flow after post-ionization of neutrals by laser beam (86). FIG. 21 is an A-A cross-section of the setup in FIG. 20. (80) are the field lines of RF-field providing trapping of ions. (212) is the flow of positive ions and attached neutrals from electrospray or API ion source. (83) are neutrals accumulated along axis of the trapping region. (84) are positive ions from the source in the trap shifted to the right from axis by DC electric field (87). (85) are positive ions' flow after post-ionization of neutrals. (88) are positive ions' flow after accumulation them from ion source in the trap (84). (89) are gas flows from mobility tubes and capillary from the ion source.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An apparatus for analyzing a flow of gaseous ions or mixture of gaseous ions and gaseous neutral species, said apparatus comprising:
   an ion mobility assembly comprising:
      an ion trapping region comprising a plurality of ion traps to receive said flow of gaseous ions or mixture of gaseous ions and gaseous neutral species;
      a plurality of parallel mobility tubes, each of said mobility tubes fluidly coupled to said ion trapping region;
      optionally, a plurality of parallel CID tubes, each of said CID tubes fluidly coupled to at least one of said mobility tubes;
      optionally, a plurality of parallel exit tubes, each of said tubes comprising at least one electrode and being fluidly coupled to at least one of said CID tubes or at least one of said mobility tubes; and,
      at least one multi-channel RF ion guide fluidly coupled to at least one of said exit tubes, at least one of said CID tubes, or at least one of said mobility tubes;
   said ion mobility assembly having a separation axis in a first direction;
   and,
   at least one TOFMS fluidly coupled to said ion mobility assembly, said TOFMS comprising a position sensitive detector.

2. The apparatus of claim 1, further comprising at least one ion mirror between said at least one multi-channel RF ion guide and said at least one TOFMS.

3. The apparatus of claim 2, wherein said at least one ion mirror comprises a conductor coated by a dielectric film.

4. The apparatus of claim 3, wherein said at least one ion mirror comprises:
   a parabolic mirror, a cylindrical parabolic minor, or a quasi-parabolic minor; and,
   a flat mirror.

5. The apparatus of claim 1, further comprising:
   a high pressure/high vacuum interface positioned between said ion mobility assembly and said at least one TOFMS; and,
   an ion interface assembly located at said high pressure/high vacuum interface.

6. The apparatus of claim 5, wherein said ion interface assembly comprises an entry electrode, one or more focusing electrode assemblies, at least one ion minor with a dielectric coating, a sectioned tube coated with a dielectric film, and a field-free tube coated with a dielectric film and having a larger diameter than said sectioned tube.

7. The apparatus of claim 1, wherein said ion mobility assembly comprises more than one ion mobility assembly and wherein one or more pairs of said more than one ion mobility assembly are opposed pairs.

8. The apparatus of claim 1, wherein a source is configured to generate said flow in a direction that is orthogonal to said first direction.

9. The apparatus of claim 8, wherein said source further comprises means for post-ionization of said gaseous ions or mixture of gaseous ions and gaseous neutral species.

10. The apparatus of claim 8, wherein said source is selected from the group consisting of a laser desorption source, a cluster bombardment source, a secondary ion source, an electrospray ionization source, photoionization source, a pneumo-spray source, an atmospheric pressure ionization source, and any combination thereof.

11. A method of analyzing a sample comprising the steps of:
   sampling a flow of gaseous ions or mixture of gaseous ions and gaseous neutral species, said flow having an axis of flow in a first direction;
   injecting said flow into an ion mobility assembly, said ion mobility assembly comprising:
   an ion trapping region comprising a plurality of ion traps to receive said flow;
   a plurality of parallel mobility tubes, each of said mobility tubes fluidly coupled to at least one of said ion traps;
   optionally, a plurality of parallel CID tubes, each of said CID tubes fluidly coupled to at least one of said mobility tubes;
   optionally, a plurality of parallel exit tubes, each of said exit tubes comprising at least one electrode and being fluidly coupled to at least one of said CID tubes or to at least one of said mobility tubes; and,
   at least one multi-channel RF ion guide fluidly coupled to at least one of said parallel exit tubes, at least one of said CID tubes, or at least one of said mobility tubes;
   said ion mobility assembly having a separation axis that is orthogonal to said first direction; and,
   thereafter injecting said flow into at least one TOFMS fluidly coupled to said ion mobility assembly, said TOFMS comprising a position sensitive detector.

12. The method of claim 11, wherein the step of creating comprises the step of applying a collimated stream of gas to said flow.

13. The method of claim 11, wherein said step of sampling comprises extracting and ionizing gaseous neutral species from a gaseous sample plume.

14. The method of claim 13, wherein said step of extracting comprises passing a collimated stream of gas through said gaseous sample plume.

15. The method of claim 13, wherein said step of ionizing comprises ionizing with laser radiation.

16. The method of claim 13, wherein said step of ionizing comprises fragmentation of neutral zwitterions.

17. The method of claim 11, wherein said method further comprises passing said flow through a differentially pumped low pressure region between said ion mobility assembly and said TOFMS.

18. The method of claim 11, wherein said step of injecting said flow through an ion mobility assembly comprises injecting said flow through more than one ion mobility assembly and wherein one or more pairs of said more than one ion mobility assembly are opposed pairs.

19. The method of claim 11, wherein said step of injecting said flow into at least one TOFMS comprises injecting said flow into at least one TOFMS comprising a multi-channel detector.

20. The method of claim 11, further comprising a step of post-ionizing neutral species in said ion trapping region with laser radiation.

21. An apparatus for analyzing a flow of gaseous ions or mixture of gaseous ions and gaseous neutral species, said apparatus comprising:
   a plurality of sources for the generation of said flow of gaseous ions or mixture of gaseous ions and gaseous neutral species,
   an ion mobility assembly comprising:
   an ion trapping region comprising a plurality of ion traps to receive said flow of gaseous ions or mixture of gaseous ions and gaseous neutral species;
   a plurality of parallel mobility tubes, each of said mobility tubes fluidly coupled to said ion trapping region;
   optionally, a plurality of parallel CID tubes, each of said CID tubes fluidly coupled to at least one of said mobility tubes;
   optionally, a plurality of parallel exit tubes, each of said tubes comprising at least one electrode and being fluidly coupled to at least one of said CID tubes or at least one of said mobility tubes; and,
   at least one multi-channel RF ion guide fluidly coupled to at least one of said exit tubes, at least one of said CID tubes, or at least one of said mobility tubes;
   said ion mobility assembly having a separation axis in a first direction;
   and,
   at least one TOFMS fluidly coupled to said ion mobility assembly, said TOFMS comprising a position sensitive detector.

22. A method of analyzing a sample comprising the steps of:
   creating a flow of gaseous ions or mixture of gaseous ions and gaseous neutral species from said sample from a plurality of sources, said flow having an axis of flow in a first direction;
   injecting said flow into an ion mobility assembly, said ion mobility assembly comprising:
   an ion trapping region comprising a plurality of ion traps to receive said flow;
   a plurality of parallel mobility tubes, each of said mobility tubes fluidly coupled to at least one of said ion traps;
   optionally, a plurality of parallel CID tubes, each of said CID tubes fluidly coupled to at least one of said mobility tubes;
   optionally, a plurality of parallel exit tubes, each of said exit tubes comprising at least one electrode and being fluidly coupled to at least one of said CID tubes or to at least one of said mobility tubes; and,
   at least one multi-channel RF ion guide fluidly coupled to at least one of said parallel exit tubes, at least one of said CID tubes, or at least one of said mobility tubes;
   said ion mobility assembly having a separation axis that is orthogonal to said first direction; and,
   thereafter injecting said flow into at least one TOFMS fluidly coupled to said ion mobility assembly, said TOFMS comprising a position sensitive detector.

* * * * *

UNITED STATES PATENT AND TRADEMARK OFFICE
CERTIFICATE OF CORRECTION

PATENT NO. : 8,115,167 B2
APPLICATION NO. : 12/338529
DATED : February 14, 2012
INVENTOR(S) : Valeriy V. Raznikov et al.

Page 1 of 1

It is certified that error appears in the above-identified patent and that said Letters Patent is hereby corrected as shown below:

Title Page, insert

--Related U.S. Application Data

(63) Continuation of Application No. 11/441,766, filed on 05/26/2006, now Pat. No. 7,482,582.-- and --(60) Provisional Application No. 60/685,247, filed on 05/27/2005.--

Signed and Sealed this
Sixth Day of August, 2013

Teresa Stanek Rea
*Acting Director of the United States Patent and Trademark Office*